(12) United States Patent
Murphy et al.

(10) Patent No.: US 9,480,773 B2
(45) Date of Patent: Nov. 1, 2016

(54) MINERALIZATION AND BIOLOGICAL MODIFICATION OF BIOMATERIAL SURFACES

(71) Applicant: THE REGENTS OF THE UNIVERSITY OF MICHIGAN, Ann Arbor, MI (US)

(72) Inventors: William L. Murphy, Ann Arbor, MI (US); Martin C. Peters, Ann Arbor, MI (US); David J. Mooney, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/724,206

(22) Filed: May 28, 2015

(65) Prior Publication Data
US 2015/0258242 A1    Sep. 17, 2015

Related U.S. Application Data

(60) Continuation of application No. 12/433,518, filed on Apr. 30, 2009, now Pat. No. 9,072,813, which is a continuation of application No. 11/441,265, filed on May 25, 2006, now abandoned, which is a continuation of application No. 10/872,199, filed on Jun. 18, 2004, now abandoned, which is a division of application No. 09/527,636, filed on Mar. 17, 2000, now Pat. No. 6,767,928.

(60) Provisional application No. 60/167,289, filed on Nov. 24, 1999, provisional application No. 60/125,118, filed on Mar. 19, 1999.

(51) Int. Cl.
| | |
|---|---|
| A61L 27/00 | (2006.01) |
| A61L 27/18 | (2006.01) |
| A61L 27/50 | (2006.01) |
| A61L 27/44 | (2006.01) |
| A61L 27/56 | (2006.01) |
| A61L 27/58 | (2006.01) |

(52) U.S. Cl.
CPC ............... *A61L 27/18* (2013.01); *A61L 27/00* (2013.01); *A61L 27/44* (2013.01); *A61L 27/50* (2013.01); *A61L 27/56* (2013.01); *A61L 27/58* (2013.01); *A61L 2400/18* (2013.01)

(58) Field of Classification Search
CPC ........ C08L 67/04; A61L 27/18; A61L 27/44; A61L 2400/18; A61L 27/00; A61L 27/50
USPC ........... 427/2.26; 514/44 R; 424/93.2, 93.21, 424/484, 486; 521/51
See application file for complete search history.

(56) References Cited

U.S. PATENT DOCUMENTS

| | | |
|---|---|---|
| 3,975,350 A | 8/1976 | Hudgin et al. |
| 4,636,526 A | 1/1987 | Dorman et al. |
| 4,933,185 A | 6/1990 | Wheatley et al. |
| 4,996,120 A | 2/1991 | Smothers et al. |
| 5,011,691 A | 4/1991 | Oppermann et al. |
| 5,041,138 A | 8/1991 | Vacanti et al. |
| 5,202,227 A | 4/1993 | Matsuda et al. |
| 5,491,198 A | 2/1996 | Shalaby et al. |
| 5,510,628 A | 4/1996 | Georger, Jr. et al. |
| 5,512,131 A | 4/1996 | Kumar et al. |
| 5,514,378 A | 5/1996 | Mikos et al. |
| 5,550,178 A | 8/1996 | Desai et al. |
| 5,554,432 A | 9/1996 | Sandor et al. |
| 5,558,517 A | 9/1996 | Shalaby et al. |
| 5,593,814 A | 1/1997 | Matsuda et al. |
| 5,639,473 A | 6/1997 | Grinstaff et al. |
| 5,641,391 A | 6/1997 | Hunter et al. |
| 5,654,381 A | 8/1997 | Hrkach et al. |
| 5,759,830 A | 6/1998 | Vacanti et al. |
| 5,763,416 A | 6/1998 | Bonadio et al. |
| 5,770,417 A | 6/1998 | Vacanti et al. |
| 5,776,748 A | 7/1998 | Singhvi et al. |
| 5,807,406 A | 9/1998 | Brauker et al. |
| 5,855,802 A | 1/1999 | Acciai et al. |
| 5,858,721 A | 1/1999 | Naughton et al. |

(Continued)

FOREIGN PATENT DOCUMENTS

| | | |
|---|---|---|
| EP | 0679373 | 11/1995 |
| EP | 0891783 | 1/1999 |

(Continued)

OTHER PUBLICATIONS

Abe, Kokubo and Yamamuro, "Apatite coating on ceramics, metals and polymers utilizing a biological process," J. Mat. Sci.: Mat. Med, 1:233-238, 1990.

Blawas and Reichert, "Protein Patterning," Biomaterials, 19:595-609, 1998.

Bonadio et al., "Localized, direct plasmid gene delivery in vivo: prolonged therapy results in reproducible tissue regeneration," Nature Medicine, 5(7):753-759, 1999.

Bradt et al., "Biomimetic mineralization of collagen by combined fibril assembly and calcium phosphate formation," Chem. Mater., 11:2694-2701, 1999.

(Continued)

*Primary Examiner* — Janet Epps-Smith
(74) *Attorney, Agent, or Firm* — Marshall, Gerstein & Borun LLP

(57) ABSTRACT

Disclosed are advantageous methods for patterning and/or mineralizing biomaterial surfaces. The techniques described are particularly useful for generating three-dimensional or contoured bioimplant materials with patterned surfaces or patterned, mineralized surfaces. Also provided are various methods of using the mineralized and/or patterned biomaterials in tissue engineering, such as bone tissue engineering, providing more control over ongoing biological processes, such as mineralization, growth factor release, cellular attachment and tissue growth.

20 Claims, 6 Drawing Sheets

(56) References Cited

U.S. PATENT DOCUMENTS

| | | | |
|---|---|---|---|
| 5,876,454 A | 3/1999 | Nanci et al. | |
| 5,885,829 A | 3/1999 | Mooney et al. | |
| 5,925,069 A | 7/1999 | Graves et al. | |
| 5,942,496 A | 8/1999 | Bonadio et al. | |
| 5,962,427 A | 10/1999 | Goldstein et al. | |
| 5,965,125 A | 10/1999 | Mineau-Hanschke | |
| 6,077,987 A | 6/2000 | Breitbart et al. | |
| 6,150,459 A | 11/2000 | Mayes et al. | |
| 6,200,646 B1 | 3/2001 | Neckers et al. | |
| 6,258,870 B1 | 7/2001 | Hubbell et al. | |
| 6,261,493 B1 | 7/2001 | Gaylo et al. | |
| 6,264,873 B1 | 7/2001 | Gigl et al. | |
| 6,294,187 B1 | 9/2001 | Boyce et al. | |
| 6,541,022 B1 | 4/2003 | Murphy et al. | |
| 6,696,073 B2 | 2/2004 | Boyce et al. | |
| 6,767,928 B1 | 7/2004 | Murphy et al. | |

FOREIGN PATENT DOCUMENTS

| | | |
|---|---|---|
| WO | WO-9423738 | 10/1994 |
| WO | WO-9717430 | 5/1997 |
| WO | WO-9844027 | 10/1998 |
| WO | WO-9958656 | 11/1999 |

OTHER PUBLICATIONS

Campbell et al., "Surface-induced mineralization: a new method for producing calcium phosphate coatings," Jrnl. Biomed. Mats. Res. 32:111-118 (1996).

Chen et al., "Geometric control of cell life and death," Science, 276(5):175-178, 1997.

Dufresne and Drier, "Optical tweezer arrays and optical substrates created with diffractive optics," Review of Scientific Instruments, 69(5):1974-1977, 1998.

Fang et al., "Stimulation of new bone formation by direct transfer of osteogenic plasmid genes," Proc. Natl. Acad. Sci. USA, 93:5753-5758, 1996.

Folch and Toner, "Cellular micropatterns on biocompatible materials," Biotechnol. Prog., 14:388-392, 1998.

Gale et al., "Fabrication of continuous-relief micro-optical elements by direct laser writing in photoresists," Optical Engineering, 33(11):3556-3566, 1994.

Gao, Niklason and Langer, "Surface hydrolysis of poly (glycolic acid) meshes increases the seeding density of vascular smooth muscle cells," J. Biomed Mater. Res., 42(3):417-424, 1998.

Gombotz and Pettit, "Biodegradable polymers for protein and peptide drug delivery," Bioconjugate Chem., 6:332-351, 1995.

Gopferich, "Bioerodible implants with programmable drug release," Jrnl. Controlled Release, 44:271-281, 1997.

Gunasekaran et al., "Mineralized Collages as a Substitute for Autograft Bone that can Deliver Bone Morphogenic Protein," 19th Ann. Meeting of the Society for Biomaterials, Apr. 28-May 2, 1993.

Gunasekaran et al., "Role of Mineralized Collagen as an Osteoconductive Biomaterial," 19th Ann. Meeting of the Society for Biomaterials, Apr. 28-May 2, 1993.

Healy et al., "Kinetics of bone cell organization and mineralization on materials with patterned surface chemistry," Biomaterials, 17(2):195-208, 1996.

Healy, Loin, and Hockberger, "Spatial distribution of mammalian cells dictated by material surface chemistry," Biotechnol. Bioeng., 43:792-800, 1994.

International Search Report for Application No. PCT/US00/07207.

International Search Report for PCT/US00/31754, mailed Aug. 6, 2001.

Ito, "Surface micropatterning to regulate cell functions," Biomaterials, 20:2333-2342, 1999.

Kaufmann et al., "Highly porous polymer matrices as a three-dimensional culture system for hepatocytes," Cell Transplantation, 6(5): 463-468, 1997.

Latour, "Molecular modeling of biomaterial surfaces," Materials Science 4:413-417 (1999).

Li, "In vitro calcium phosphate formation on a natural composite material, bamboo," Biomaterials, 18:389-395 (1997).

Li, Bakker and van Blitterswijk, "The bone-bonding polymer polyactive® 80/20 induces hydroxycarbonate apatite formation in vitro," J. Biomed. Mat. Res., 34:79-86, 1997.

Mait, "Diffractive Beauty," Optics and Photonics News, 9(11): 21-25, 52, 1998.

Mikos et al., "Prevascularization of porous biodegradable polymers," Biotechnol. Bioeng., 42:716-723, 1993.

Miyaji et al., "Bonelike apatite coating on organic polymers: Novel nucleation process using sodium silicate solution," Biomaterials, 20:913-919, 1999.

Mooney and Vacanti, "Tissue engineering using cells and synthetic polymers, " Transplantation Reviews, 7(3):153-162, 1993.

Mooney et al., "Novel approach to fabricate porous sponges of poly(D,L-lactic-co-glycolic acid) without the use of organic solvents," Biomaterials, 17(14):1417-1422, 1996.

Mooney et al., "Patterning of functional antibodies and other proteins by photolithography of silane monolayers," Proc. Natl. Acad. Sci. USA, 93(10):12287-12291, 1996.

Murphy, Kohn and Mooney, "Growth of continuous bonelike mineral within porous poly(lactide-co-glycolide) scaffolds in vitro," J. Biomed Mater. Res., 50(1):50-58, 2000.

Nicolau et al. "Patterning neuronal and glia cells on light-assisted functionalized photoresists," Biosensor & Bioelectronics, 14:317-325 (1999).

Nicolau et al. "Protein patterning via radiation-assisted surface functionalization of conventional microlithographic materials," Engineering Aspects, 51-52 (1999).

Niino and Yabe, "Excimer laster ablation of polyethersulfone derivatives: periodic morphological micro-modification on ablated," A: Chem, 65:303-312 (1992).

Peters and Mooney, "Growth factor delivery from tissue engineering matrices: Inducing angiogenesis to enhance transplanted cell engraftment," In: Controlled Drug Delivery: Designing Technologies for the Future, Park and Mrsny, Eds., Washington, D.C., American Chemical Society, Ch. 16, p. 157-166, 2000.

Putnam and Mooney, "Tissue engineering using synthetic extracellular matrices," Nature Medicine, 2(7):824-826, 1996.

Putney and Burke "Improving protein therapeutics with sustained-release formulations," Nature Biotechnology 16: 153-157, 1998.

Reis, J. of Materials in Medicine, 8:897-905 (1997).

Shea et al., "DNA delivery from polymer matrices for tissue engineering," Nature Biotechnology, 17(6):551-554, 1999.

Sheridan et al., "Bioabsorbable polymer scaffolds for tissue engineering capable of sustained growth factor delivery," Journal of Controlled Release, 64:91-102, 2000.

Singhvi et al., "Engineering cell shape and function," Science, 264(4):696-698,1994.

Taguchi et al., "A study on hydroxyapatite formation on/in the hydroxyl groups-bearing nonionic hydrogels," J. Biomater. Sci. Polymer Edn., 10(1): 19-32, 1999.

Tanahashi et al., "Surface functional group dependence on apatite formation on self-assembled monolayers in a simulated body fluid," J. of Biomedical Materials Research 34:305-315 (1997).

Thomas, et al., "The role of vitronectin in the attachment and spatial distribution of bone derived cells on materials with patterned surface chemistry," J. Biomed Mater. Res., 37:81-93, 1997.

Varma et al., "Porous calcium phosphate coating over phosphorylated chitosan film by a biomimetic method," Biomaterials, 20:879-884, 1999.

Wen et al., "Preparation of calcium phosphate coating on titanium implant materials by simple chemistry," J. Biomed. Mater. Res., 41:227-236, 1998.

Zhang and Ma, "Porous poly(L-lactic acid)/apatite composites created by biomimetic process," J Biomed Mater. Res., 45:285-293, 1999.

Zhang et al., "Biological surface engineering: A simple system for cell pattern formation," Biomaterials, 20:1213-1220, 1999.

MINERALIZATION AND BIOLOGICAL MODIFICATION OF BIOMATERIAL SURFACES

The present application claims priority to second U.S. provisional application Ser. No. 60/167,289, filed Nov. 24, 1999, which claims priority to first U.S. provisional application Ser. No. 60/125,118, filed Mar. 19, 1999, the entire text and figures of which applications are incorporated herein by reference without disclaimer.

The U.S. Government owns rights in the present invention pursuant to grant numbers R01 DE13033 and T32 GM 08353 from the National Institutes of Health.

BACKGROUND OF THE INVENTION

1. Field of the Invention

The present invention relates generally to the diverse fields of lithography, chemistry, biomaterials and tissue engineering. More particularly, it concerns the patterning and/or mineralization of biopolymers. These methods provided are particularly suited to the generation of surface-modified three-dimensional biomaterials for use in cell culture, transplantation and tissue engineering.

2. Description of Related Art

Many biomedical procedures require the provision of healthy tissue to counteract the disease process or trauma being treated. This work is often hampered by the tremendous shortage of tissues available for transplantation and/or grafting. Tissue engineering may ultimately provide alternatives to whole organ or tissue transplantation.

In order to generate engineered tissues, various combinations of biomaterials and living cells are currently being investigated. Although attention is often focused on the cellular aspects of the engineering process, the design characteristics of the biomaterials also constitute a major challenge in this field.

In recent years, the ability to regenerate tissues and to control the properties of the regenerated tissue have been investigated by trying to specifically tune the mechanical or chemical properties of the biomaterial scaffold (Kim et al., 1997; Kohn et al. 1997). The majority of this work has involved the incorporation of chemical factors into the material during processing, or the tuning of mechanical properties by altering the constituents of the material.

The foregoing methods have been used in an attempt to utilize chemical or mechanical signaling to affect changes in the proliferation and/or differentiation of cells during tissue regeneration. Despite such efforts, there remains in the art a need for improved biomaterials, particularly those with a better capacity to support complex tissue growth in vitro (in cell culture) and in vivo (upon implantation).

SUMMARY OF THE INVENTION

The present invention overcomes various drawbacks in the art by providing a range of improved methods, compositions and devices for use in cell culture, cell transplantation and tissue engineering. The methods, compositions and apparatus of the invention involve patterned and/or mineralized biomaterial surfaces. The techniques and products provided are particularly useful for generating three-dimensional or contoured bioimplant materials with modified surface features and for generating biomaterials incorporating bioactive factors and/or cells. The various methods of using the mineralized and/or patterned biomaterials in tissue engineering, including bone tissue engineering and vascularization, thus provide more control over the biological processes.

Unifying aspects of the invention involve the surface modification, functionalization or treatment of biocompatible materials. Such modifications, functionalizations or treatment methods are preferably used to create reactive surfaces that may be further manipulated, e.g., patterned and/or mineralized. The patterned and/or mineralized biocompatible materials have a variety of uses, both in vitro and in vivo.

A first general aspect of the present invention concerns the patterned treatment of polymer biomaterial surfaces using a unique "diffraction lithography" process. Prior lithographic methods of surface patterning have been limited to flat, two dimensional surfaces, which is a significant limitation overcome by the methods provided herein. The present invention is thus applicable to surface patterning on complex three dimensional biomaterials with surface contours.

The development of these aspects of the overall invention is particularly surprising as it provides patterns of sufficient resolution to be useful in biological embodiments. Further advantages of the invention over the methods of the prior art include the ready incorporation of biologically active components into the patterned biomaterials and the reduced risk of contamination. Other significant features of the invention are the cost-effectiveness and labor-saving nature of the techniques.

A second general aspect of the invention involves the surface treatment or functionalization of a biocompatible material, preferably a porous, degradable polymer, such as a film or sponge, to spur nucleation and growth of an extended mineral layer on the surface. Such treatment can be controlled to provide a homogeneous surface mineral layer or a patterned mineral layer, such as islands of minerals. Each of such extended mineral layers allow the growth of continuous bone-like mineral layers, even on inner pore surfaces of polymer scaffolds.

Such extensively mineralized, patterned mineralized and/or hypermineralized polymers of the invention have advantageous uses in bone tissue engineering and regeneration and tissue vascularization. The formation of extended mineral islands and/or substantially homogeneous, "continuous" mineral layers, particularly those on the inner pore surfaces of three dimensional matrices, is advantageous as it can be achieved simply (a one step incubation), quickly (about five days), at room temperature, without leading to an appreciable decrease in total scaffold porosity or pore size, and is amenable to further incorporation of bioactive substances.

The further incorporation of bioactive substances is exemplified by the formation and use of polymers, preferably, biodegradable polymers, that are both mineralized and provide for the sustained release of bioactive factors, such as protein growth factors. In these aspects of the invention, the type of mineral layer may be controlled by altering the molecular weight of the polymer; the composition of the polymer; the processing technique (solvent casting, heat pressing, gas foaming) used to prepare the polymer; the type and/or density of defects on the polymer surface; and/or by varying the incubation time.

The various improved biomaterials of the invention have advantageous uses in cell and tissue culture and engineering methods, both in vitro and in vivo. By way of example only, the present invention provides biomaterial methods and compositions with patterned mineral surfaces for use in patterning bone cell adhesion.

Accordingly, the general methods of the invention are those suitable for the surface-modification of at least a first biocompatible material or device, comprising:

(a) generating a patterned surface on a biocompatible material or device by a method comprising irradiating at least a first photosensitive surface of a biocompatible material or device with pre-patterned electromagnetic radiation, thereby generating a pattern on at least a first surface of the biocompatible material or device; and/or (b) generating an extended mineralized surface on a biocompatible material or device by a method comprising functionalizing at least a first surface of a biocompatible material or device and contacting the functionalized surface with an amount of a mineral-containing solution, thereby generating extended mineralization on at least a first surface of the biocompatible material or device.

The irradiation, lithographic or diffractive lithography methods generally comprise generating a patterned surface on a biocompatible material by a method comprising functionalizing at least a first photosensitive surface of a biocompatible material by irradiating the photosensitive surface with an amount of pre-patterned electromagnetic radiation effective to generate a patterned biocompatible material comprising a pattern on at least a first surface of the biocompatible material. In these methods, the functionalized surface is preferably functionalized to create a plurality of polar oxygen groups at the surface, generally so that the functionalized surface can be further modified, e.g., with minerals, cells or the like.

It will thus be noted that the methods for generating a patterned surface on a biomaterial or device, comprise "directly" applying pre-patterned radiation to a photosensitive surface of a biomaterial or device. The "direct" application of the pre-patterned radiation is a significant advantage as it occurs without the intervention of a "mask", which is a significant drawback in contact lithography. The present invention thus provides "mask-less" or "naked" lithography for biomaterial patterning in which pre-patterned radiation is impinging directly onto a photosensitive surface of a biomaterial in the absence of an intervening mask.

"Electromagnetic radiation", as used herein, includes all types of radiation being electromagnetic in origin, i.e., being composed of perpendicular electric and magnetic fields. The pre-patterned radiation for use in the invention is preferably constructively and destructively interfering electromagnetic radiation.

The present invention includes the use of all constructively and destructively interfering radiation, such as constructive and destructive interference based on amplitude, as well as phase holograms that rely on constructive and destructive interference based on phase only. One advantage of phase only holograms is that more light gets through, and a more complex pattern can be formed. However, the use of diffraction gratings to provide constructive and destructive interference based on amplitude is advantageous in construction and cost.

The pre-patterned radiation may be constructively and destructively interfering radiation from any effective part of the visible spectrum. Constructively and destructively interfering radiation in the UV, infrared and visible spectra are preferred examples, with UV and visible spectra being most preferred.

The pre-patterned, constructively and destructively interfering radiation may be generated by impinging monochromatic radiation on a diffractive optical element that converts the monochromatic radiation into constructively and destructively interfering radiation.

The monochromatic radiation may be generated from any suitable source. For example, one or more lasers or one or more mercury bulbs. The monochromatic radiation may be first generated from an electromagnetic radiation source and then passed through a suitable filter.

A wide range of diffractive optical elements may be used in the invention. "Diffractive optical element" is a term that includes diffraction gratings, holograms, and other pattern generators. There is virtually no limitation to these aspects of the invention as any component of the spectrum can be patterned by any type of optical element by varying the design of the optical element. For example, there is a well defined relationship between the feature spacing in a diffraction pattern, and the spacing of the slits in the diffraction pattern plus the wavelength of the radiation. Thus, the slit widths can be varied to create any pattern spacing with any wavelength of radiation.

Therefore, one may use in the invention one or more diffractive lenses, deflector/array generators, hemispherical lenslets, kinoforms, diffraction gratings, fresnel microlenses and/or a phase-only holograms. Those of ordinary skill in the art will understand that a "diffraction grating" actually produces an "interference pattern", not a "diffraction pattern", which is a matter of semantics resulting from the original naming of "diffraction gratings".

The diffractive optical element(s) may also be fabricated from any suitable material, such as a transparent polymer or glass. Examples of transparent polymers are those selected from the group consisting of a poly(methyl methacrylate), poly(styrene), and a high density poly(ethylene). Examples of diffraction gratings are those fabricated from metal on glass, metal on polymer or metal with transmission apertures (slits or holes). Other suitable diffractive optical elements are those fabricated from fused silica or sapphire. The choice of element and matching of element to processing conditions will be routine to those of skill in the art.

Those of ordinary skill in the art will understand that UV light is less suitable for use with cells. When using visible light, no compromise of cell function is expected. Solely as a precaution, an upper limit may be about 6 $W/cm^2$ (Watts per square centimeter). For infrared light, a precautionary upper limit may be about 2.2 $MW/cm^2$ (Megawatts per square centimeter).

For use with proteins, a precautionary upper limit of UV may be about 8 $mW/cm^2$ (Milliwatts per square centimeter). It is not believed that an upper limit of intensity of visible light limits the application of the present invention to use with proteins. For use with proteins and cells, local heating during polymerization can be readily minimized, e.g., by using high molecular weight resins, and by decreasing total polymerization time.

Generating a pattern with pre-patterned electromagnetic radiation includes the direct generation of a patterned surface that naturally occurs as a result of the electromagnetic radiation contacting the surface of the biocompatible material. Therefore, the "photosensitive surface" of the biocompatible material may simply be the "unmodified" biocompatible material surface. The "thereby generating" of the method can therefore be an inherent feature of the method.

"Thereby generating" may also include methods where the irradiated photosensitive surface is "developed" to provide the patterned surface. Where the photosensitive surface has not been coated with any particular photosensitive material, the generation of the patterned surface after irradiation preferably includes "developing" the irradiated photosensitive biomaterial to generate the patterned surface. "Developing" in this sense preferably involves washing or rinsing in a suitable liquid or solvent, such as water or an organic solvent.

The invention further includes more indirect methods of generating the patterned surface, i.e., where the photosensitive surface to be irradiated is not the unmodified biomaterial surface. In such methods, the photosensitive surface is prepared by applying a photosensitive composition, admixture, combination, coating or layer to at least a first surface of the biocompatible material.

The photosensitive composition may be applied to at least a first surface of the biocompatible material by contacting the biocompatible material with a formulation of the photosensitive composition in a volatile solvent and evaporating the solvent to coat the photosensitive composition onto the at least a first surface. The photosensitive composition may also be applied to at least a first surface of the biocompatible material by contacting the biocompatible material with a formulation of the photosensitive composition in an aqueous or colloidal solution to adsorb the photosensitive composition onto the at least a first surface.

The invention thus comprises:
(a) applying a photosensitive layer to at least a first surface of a biomaterial;
(b) creating pre-patterned radiation;
(c) irradiating the photosensitive layer with the pre-patterned radiation to form an irradiated layer; and
(d) developing the irradiated layer to generate a pattern on the at least a first surface of the biomaterial.

The invention further comprises:
(a) applying a photosensitive layer to at least a first surface of a biomaterial;
(b) obtaining a monochromatic radiation source;
(c) impinging the monochromatic radiation source on an element that converts the monochromatic radiation into patterned radiation;
(d) irradiating the photosensitive layer with the patterned radiation to form an irradiated layer; and
(e) developing the irradiated layer to generate a pattern on the at least a first surface of the biomaterial.

The invention still further comprises:
(a) applying a photosensitive layer to at least a first surface of a biomaterial;
(b) obtaining a monochromatic radiation source;
(c) transmitting the monochromatic radiation source through an element that transforms the monochromatic radiation into patterned radiation;
(d) impinging the transmitted patterned radiation onto the photosensitive layer of the biomaterial to form an irradiated layer; and
(e) developing the irradiated layer to generate a pattern on the at least a first surface of the biomaterial.

Any one of a wide variety of photosensitive compositions may be used. Such compositions generally comprise a combined effective amount of at least a first photoinitiator and at least a first polymerizable component.

Suitable photosensitive compositions may comprise a polymerization-initiating amount of at least a first UV-excitable photoinitiator, such as a UV-excitable photoinitiator selected from the group consisting of a benzoin derivative, benzil ketal, hydroxyalkylphenone, alpha-amino ketone, acylphosphine oxide, benzophenone derivative and a thioxanthone derivative.

Other photosensitive compositions may comprise a polymerization-initiating amount of at least a first visible light-excitable photoinitiator, such as a visible light-excitable photoinitiator selected from the group consisting of eosin, methylene blue, rose bengal, dialkylphenacylsulfonium butyltriphenylborate, a fluorinated diaryltitanocene, a cyanine, a cyanine borate, a ketocoumarin and a fluorone dye. These photosensitive compositions may further comprise a co-initiating amount of at least a first co-initiator or accelerator, such as a co-initiator or accelerator selected from the group consisting of a tertiary amine, peroxide, organotin compound, borate salt and an imidazole.

The choice of components for use in the photosensitive compositions will be straightforward to those of skill in the art. Essentially any photoinitiator or initiator system and any "resin" (types of components or monomers to be photopolymerized) can be combined. The choice of resin is therefore wide. For example, a suitable "multifunctional acrylate" is any monomer that can be acrylated.

The resin components are used in photopolymerizable amounts, such as photopolymerizable amounts of at least a first monomeric, oligomeric or polymeric polymerizable component. Suitable polymerizable monomers include those selected from the group consisting of an unsaturated fumaric polyester, maleic polyester, styrene, a multifunctional acrylate monomer, an epoxide and a vinyl ether.

One currently preferred photosensitive composition comprises a combined effective amount of an eosin photoinitiator, a poly(ethylene glycol) diacrylate polymerizable component and a triethanolamine accelerator.

The methods of the invention produce patterns with a resolution of between about 1 µM and about 500 µM; of between about 1 µM and about 100 µM; of between about 10 µM and about 100 µM; of between about 1 µM and about 10 µM; and of between about 10 µM and about 20 µM. These are highly suitable for biomedical embodiments, although substantially unsuitable for microelectronic embodiments, as a single cell is in the 10 µM to 20 µM range. Patterns with a resolution of about 0.5, 0.75, 1, 2, 3, 4, 5, 6, 7, 8, 9, 10, 12, 15, 20, 25, 50, 75, 100, 150, 200, 250, 300, 350, 400, 450, 500, 550 or about 600 µM or so can be produced and used to advantage.

An advantage of the invention is that the entire processes can be carried out at biocompatible temperatures. For example, a biocompatible material can be maintained on a temperature-controlled support during irradiation.

The biocompatible materials, either before, during or after patterning, may be contacted with an amount of a mineral-containing solution effective to generate some, moderate, or preferably extended mineralization on at least a first surface of the biocompatible material. Such methods link to the mineralization methods and comprise contacting with a mineral-containing solution prior.

Preferably, the biocompatible material is contacted with the mineral-containing solution during or subsequent to the generation of the patterned surface, thereby forming a mineralized biocompatible material comprising a pattern of minerals on least a first surface. Furthermore, at least a first mineral-adherent biological cell may be subsequently bound to the mineralized biocompatible material to form a pattern of biological cells on least a first surface of the biocompatible material.

Both the mineral adherence and/or cell adherence may be carried out by exposure of the biocompatible material and/or mineralized biocompatible material to a population of minerals and/or cells either in vitro or in vivo. Sequential or simultaneous exposure may be used.

In the mineralization methods of the invention, one generates an extended mineralized surface on a biocompatible material by a method comprising functionalizing at least a first surface of a biocompatible material to create a plurality of polar oxygen groups at a functionalized surface and contacting the functionalized surface with an amount of a mineral-containing solution effective to generate extended mineralization on the at least a first surface of the biocompatible material.

The methods may comprise generating the functionalized surface by exposing at least a first surface of the biocompatible material to a functionalizing pre-treatment prior to contact with the mineral-containing solution. Effective functionalizing pre-treatments include exposure to an effective amount of electromagnetic radiation, such as UV radiation; exposure to an effective amount of electron beam (e-beam) irradiation; and exposure to functionalizing biocompatible chemicals, such as an effective amount of a NaOH solution.

The methods also comprise one-step methods wherein the functionalized surface is generated during the contact with the mineral-containing solution. Such single step methods for forming a mineralized biomaterial that comprises an extended mineral coating on a biomaterial surface comprise incubating a mineralizable biomaterial with an amount of a mineral-containing solution, such as an aqueous mineral solution, effective to generate a functionalized biomaterial surface upon which an extended mineral coating forms during the incubation. These methods are preferred for use with polymer or copolymer biomaterials, such as polylactic acid (PLA) polymer, polyglycolic acid (PGA) polymer or polylactic-co-glycolic acid (PLG) copolymer biomaterials.

Any mineralization method, whether pre-patterned or not, may use a mineral-containing solution that comprises calcium, wherein the resultant mineralization or extended mineralization comprises an extended calcium coating. Mineral-containing solutions may also comprise at least a first and second mineral, wherein the resultant mineralization or extended mineralization comprises a mixture of the first and second minerals. Mineral-containing solutions may further comprise a plurality of distinct minerals, wherein the resultant mineralization or extended mineralization comprises a heterogeneous polymineralized coating.

The methods are controllable to provide mineralization, extended mineralization, patterned mineralization, extended patterned mineralization, substantially homogeneous mineral coatings, hypermineralized portions or regions, inner pore surfaces of porous materials wherein a mineral or an extended mineral coating is generated on the inner pore surface, and/or pluralities of discrete mineral islands.

Methods for controlling the surface mineralization of biomaterial polymers comprise altering the molecular weight, polymer composition, ratio of components within the polymer, fabrication technique or surface properties of the biomaterial polymer prior to executing at least a first surface mineralization process. The methods allow control of the type of surface mineralization and the degree of surface mineralization, exemplified by the number or size of mineral islands at the surface of the biomaterial polymer.

In one example, the biomaterial polymer is a polylactic-co-glycolic acid copolymer biomaterial and the ratio of lactide and glycolide components within the copolymer composition is altered. In another example, at least a first surface property of the polymer composition is altered. Further, controlled surface defects may be provided to the polymer composition to provide a controlled nucleation of discrete mineral islands at the surface of the biomaterial polymer. The density of such surface defects may be altered.

The time period of the surface mineralization process may also be altered. For example, the time of the surface mineralization process may be extended until discrete mineral islands at the surface of the biomaterial polymer expand to form a substantially homogeneous mineral coating at the surface of the biomaterial polymer.

In all such methods, the mineral-containing solution may be a body fluid or a synthetic medium that mimics a body fluid. The biocompatible material may be contacted with the mineral-containing solution by exposure to a natural or synthetic mineral-containing solution in vitro or to a mineral-containing body fluid in vivo.

Any of the foregoing methods, whether for patterning or mineralization or both, are suitable for direct use with, or for adaptation for use with, virtually any biocompatible material or device. For example, the biocompatible materials may comprise at least a first portion that is biodegradable, non-biodegradable, 3-dimensional, scaffold-like, substantially 2-dimensional, 2-dimensional or film-like. The biocompatible materials may comprise at least a first portion that has an interconnected or open pore structure.

The biocompatible materials may further comprise at least a first portion that is fabricated from metal, bioglass, aluminate, biomineral, bioceramic, titanium, biomineral-coated titanium, hydroxyapatite, carbonated hydroxyapatite, calcium carbonate, or from a naturally-occurring or synthetic polymer portion. The polymers may be selected from collagen, alginate, fibrin, matrigel, modified alginate, elastin, chitosan, gelatin, poly(vinyl alcohol), poly(ethylene glycol), pluronic, poly(vinylpyrollidone), hydroxyethyl cellulose, hydroxypropyl cellulose, carboxymethyl cellulose, poly(ethylene terephthalate), poly(anhydride), poly(propylene fumarate), a polymer enriched in carboxylic acid groups, polylactic acid (PLA) polymer, polyglycolic acid (PGA) polymer, polylactic-co-glycolic acid (PLG) copolymer and PLG copolymers having a ratio of about 85 percent lactide to about 15 percent glycolide.

The biocompatible materials may further comprise at least a first portion that is prepared by a process comprising gas foaming and particulate leaching, optionally wherein at least a first bioactive substance is operatively associated with the biocompatible material during the gas foaming and particulate leaching process.

The gas foaming and particulate leaching process may comprise the steps of:
 (a) preparing an admixture at least comprising a leachable particulate material and particles capable of forming a porous, degradable polymer biomaterial;
 (b) subjecting the admixture to a gas foaming process to create a porous, degradable polymer biomaterial that comprises the leachable particulate material; and
 (c) subjecting the porous, degradable polymer biomaterial to a leaching process that removes the leachable particulate material from the porous, degradable polymer biomaterial, thereby creating additional porosity.

The leaching process may comprise contacting the porous, degradable polymer biomaterial with a mineral-containing leaching material.

The biocompatible materials may further comprise at least a first portion that is a substantially level surface or a contoured surface. As such, the biocompatible material may be fabricated as at least a portion of an implantable device.

The foregoing methods and resultant biocompatible materials and devices may further comprise a biologically effective amount of at least a first bioactive substance, bioactive drug or biological cell, two such bioactive substances, drugs or biological cells or a plurality of such bioactive substances, drugs or biological cells.

Patterned biocompatible materials may thus be exposed to at least a first binding-competent mineral, bioactive substance or biological cell, thereby forming a biocompatible material comprising a mineral, bioactive substance or biological cell bound in a pattern to at least a first surface thereof. Any resultant patterned mineralized biocompatible materials may be exposed to at least a first mineral-adherent cell, thereby forming a mineralized biocompatible material comprising at least a first cell bound in a pattern to at least a first surface of said biocompatible material.

Growth factors and/or adhesion ligands may be used to forming growth factor- or adhesion ligand-coated biocompatible materials comprising at least a first growth factor or adhesion ligand bound in a pattern to at least a first surface of said biocompatible material. Such growth factor- or adhesion ligand-coated biocompatible material may be exposed to at least, a first growth factor- or adhesion ligand-adherent cell, thereby forming a mineralized biocompatible material comprising at least a first cell bound in a pattern to at least a first surface of said biocompatible material.

The bioactive substance(s) include DNA molecules, RNA molecules, antisense nucleic acids, ribozymes, plasmids, expression vectors, viral vectors, recombinant viruses, marker proteins, transcription or elongation factors, cell cycle control proteins, kinases, phosphatases, DNA repair proteins, oncogenes, tumor suppressors, angiogenic proteins, anti-angiogenic proteins, cell surface receptors, accessory signaling molecules, transport proteins, enzymes, anti-bacterial agents, anti-viral agents, antigens, immunogens, apoptosis-inducing agents, anti-apoptosis agents and cytotoxins.

The bioactive substance(s) further include hormones, neurotransmitters, growth factors, hormone, neurotransmitter or growth factor receptors, interferons, interleukins, chemokines, cytokines, colony stimulating factors, chemotactic factors, extracellular matrix components, and adhesion molecules, ligands and peptides; such as growth hormone, parathyroid hormone (PTH), bone morphogenetic protein (BMP), transforming growth factor-$\alpha$ (TGF-$\alpha$), TGF-$\beta$1, TGF-$\beta$2, fibroblast growth factor (FGF), granulocyte/macrophage colony stimulating factor (GMCSF), epidermal growth factor (EGF), platelet derived growth factor (PDGF), insulin-like growth factor (IGF), scatter factor/hepatocyte growth factor (HGF), fibrin, collagen, fibronectin, vitronectin, hyaluronic acid, an RGD-containing peptide or polypeptide, an angiopoietin and vascular endothelial cell growth factor (VEGF).

The biologic cells include bone progenitor cells, fibroblasts, endothelial cells, endothelial cell precursors, stem cells, macrophages, fibroblasts, vascular cells, osteoblasts, chondroblasts, osteoclasts and recombinant cells that express exogenous nucleic acid segment(s) that produce transcriptional or translated products in the cells.

The biocompatible materials may further comprise a combined biologically effective amount of at least a first bioactive substance and at least a first biological cell. For example, a combined biologically effective amount of at least a first osteotropic growth factor or osteotropic growth factor nucleic acid and a cell population comprising bone progenitor cells; or a combined biologically effective amount of VEGF or a VEGF nucleic acid and a cell population comprising.

The at least a first bioactive substance, drug or biological cell may be incorporated into the biocompatible material prior to, during or subsequent to the surface-modification process. The incorporation into patterned surface(s) is an advantage as the bioactive substance, drug or biological cell is bound in a pattern at the patterned surface. The biocompatible material may comprise at least a first mineralized surface, wherein a mineral-adherent bioactive substance, drug or biological cell may be bound to the mineralized surface.

The present invention further covers all surface-modified biocompatible materials, kits, structures, devices and implantable biomedical devices with at least a first portion made by any of the foregoing methods, process or means and combinations thereof. Such surface-modified biocompatible materials may be used in cell culture, cell transplantation, tissue engineering and/or guided tissue regeneration and in the preparation of one or more medicaments or therapeutic kits for use for treating a medical condition in need of cell transplantation, tissue engineering and/or guided tissue regeneration.

Methods of the invention include those for culturing cells, comprising growing a cell population in contact with a surface-modified biocompatible material in accordance with the present invention. The cell population may be maintained in contact with the surface-modified biocompatible material under conditions and for a period of time effective to generate a two or three dimensional tissue-like structure, such as a bone-like tissue or neovascularized or vascularized tissue.

Such methods may be executed in vitro or in vivo. The cultured cells may be separated from a surface-modified biocompatible material and provided to an animal, or may be provided to an animal whilst still in contact with the surface-modified biocompatible material.

Further methods include those for transplanting cells into an animal, comprising applying to a tissue site of an animal a biologically effective amount of a cell-biocompatible material composition that comprises a cell population in operative association with a surface-modified biocompatible material in accordance with the present invention.

Still further methods are those for tissue engineering in an animal, comprising applying to a tissue progenitor site of an animal a biologically effective amount of a biocompatible material composition that provides a scaffold for tissue growth and that comprises a surface-modified biocompatible material in accordance with the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
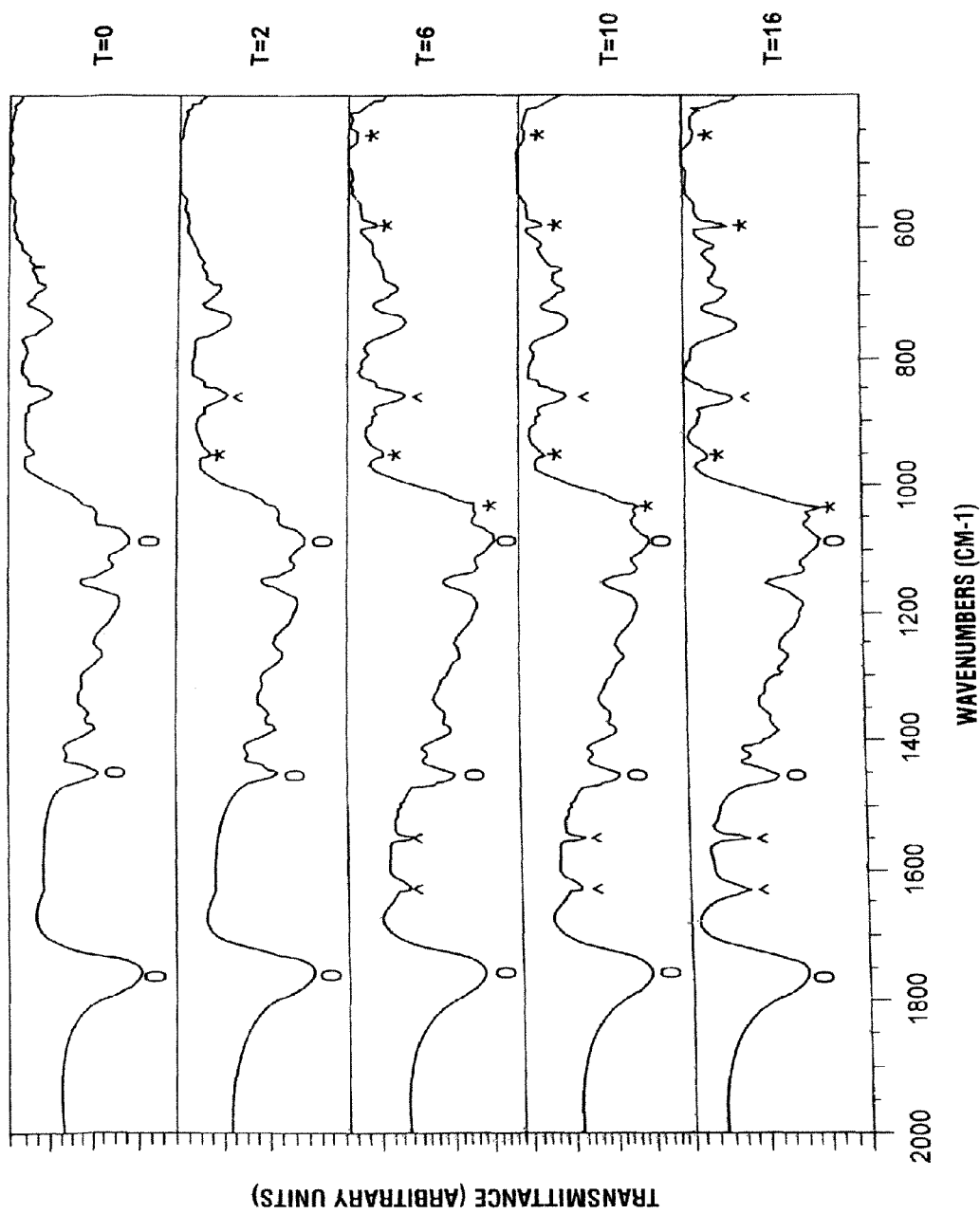
FIG. 1. FTIR spectra displaying development of phosphate (*) and carbonate (^) peaks with increasing incubation time in SBF. Peaks representing Poly(lactic-co-glycolic acid) are also labelled (o). Incubation times are given to the right of each spectrum.

Orthopaedic tissue engineering strategies have often focused on the use of natural or synthetic, degradable materials as scaffolds for cell transplantation (cell-based strategies) (Langer and Vacanti, 1993; Crane et al., 1995; Putnam and Mooney, 1996) or as a means to guide regeneration by native osteogenic cells (conductive strategies) (Minabe, 1991). Conductive and cell transplantation strategies have been somewhat effective in bone tissue engineering (Ripamonti, 1992; Ishaug-Riley, 1997; Shea et al., "Bone formation from pre-osteoblasts on 3-D scaffolds," Submitted). The degree of success of these tissue engineering methods is dependent on the properties of the scaffold.

Basic scaffold design requirements include degradability, biocompatibility, high surface area/volume ratio, osteoconductivity, and mechanical integrity. A biocompatible scaffold material that is degradable over a controllable time scale into non-toxic degradation products may disappear in concert with new tissue formation, leaving a natural tissue replacement. A high surface area/volume ratio allows for mass transport between cells within the scaffold and the surrounding host tissue, and provides space for ingrowth of fibrovascular tissue.

Osteoconductivity is important for binding and migration of transplanted and/or native osteogenic cells. Mechanical integrity is required to withstand cellular contractile forces during tissue development to ensure maintenance of the initial shape of the scaffold (Kim and Mooney, 1998).

The degradability, biocompatibility, and large surface area/volume ratio of scaffolds can be accomplished by the appropriate choice of synthetic or natural material and processing approach. Poly(lactic acid), poly(glycolic acid), and their copolymers have been used in tissue engineering applications because they undergo controllable hydrolytic degradation into natural metabolites (Gilding, 1981; Li et al., 1990), and can be processed into highly porous scaffolds by a variety of methods (Harris et al., 1998; Lo et al., 1995; Mikos and Thorsen, 1994).

A limitation in engineering of many tissue types, including bone tissue, is the inability to induce rapid vascular ingrowth during tissue development (Mooney et al., 1997). The viability of transplanted cells and/or host cells that migrate into the scaffold from the native tissue is dependent on transport of nutrients and waste products between the cells and the host tissue.

Transport is initially due solely to diffusion, and cells more than several hundred microns from blood vessels in the surrounding tissue either fail to engraft or rapidly die due to oxygen deprivation (Colton, 1995). Studies indicate that blood vessels will infiltrate a macroporous scaffold to provide enhanced transport to engineered tissues, but the process occurs at a rate of less than 1 mm per day and it typically takes one to two wk for complete penetration of vascular tissue into relatively thin (e.g., 3 mm thick) scaffolds (Mikos et al., 1993; Mooney et al., 1994).

The present invention provides improved biomaterials for use in tissue engineering. Various of the foregoing drawbacks are overcome by the developments of the invention. Certain materials provided are biodegradable, porous polymers with homogeneous surface layers of minerals and mineralized inner pores. Porous polymer materials are also provided that have continuous mineral layers in combination with bioactive factors. Other materials provided are patterned materials, to which any mineral and/or biological component may be bound in a spatially controlled manner.

The patterned and/or mineralized polymers with bioactive factors are provided to give more control over, or to augment, the processes of tissue formation and regeneration. For example, growth factors can be used that induce cells to behave in a specific manner (Giannobile, 1996). Several factors have been identified that induce chemotaxis, proliferation, differentiation, and matrix synthesis of specific cell types, any one or more of which may be used in the present invention.

Although certain systems have been proposed for factor delivery (Langer, 1990; Whang et al., 1998; Wheeler et al., 1998; Shea et al., 1999; Sheridan et al., *J. Cont. Rel.*, In Press), macroporous tissue engineering matrices are still in need of improvement. The inventors reasoned that the inclusion of bioactive factors into a scaffold would allow a higher level of control over cell function within and adjacent to a scaffold construct, thus addressing specific limitations in conductive and cell-based tissue engineering methods.

Certain aspects of the present invention therefore provide scaffolds that combine the degradability, biocompatibility and osteoconductivity mineralized scaffolds with the tissue inductive properties of bioactive polypeptides. Patterning provides an additional degree of control. The invention achieves the growth of bone-like mineral on the inner pore surfaces of a scaffold containing a growth factor without compromising factor bioactivity or scaffold porosity. The growth factor is exemplified by vascular endothelial cell growth factor (VEGF), a potent mitogen for human micro and macrovascular endothelial cells, which does not exhibit mitogenic effects on other cell types (Leung et al., 1989).

The mineral- and VEGF-containing matrices of the present invention are particularly contemplated for use in inducing neovascularization concurrent with the engineering of bone tissue. Enhanced vascular tissue formation during tissue development will lead to enhanced viability of native and/or transplanted osteogenic cells within a scaffold, enabling the engineering of a larger volume of bone tissue.

Other bioactive factors for use in this invention include growth hormone (GH); parathyroid hormone (PTH), including PTH1-34); bone morphogenetic proteins (BMPs), such as BMP-2A, BMP-2B, BMP-3, BMP-4, BMP-5, BMP-6, BMP-7 and BMP-8; transforming growth factor-α (TGF-α), TGF-β1 and TGF-β2; fibroblast growth factor (FGF); granulocyte/macrophage colony stimulating factor (GMCSF); epidermal growth factor (EGF); platelet derived growth factor (PDGF); an insulin-like growth factor (IGF) and leukemia inhibitory factor (LIF).

In fact, virtually any hormone, neurotransmitter, growth factor, growth factor receptor, interferon, interleukin, chemokine, cytokine, colony stimulating factor and/or chemotactic factor protein or polypeptide may be employed. Further examples include transcription or elongation factors, cell cycle control proteins, kinases, phosphatases, DNA repair proteins, oncogenes, tumor suppressors, angiogenic proteins, anti-angiogenic proteins, immune response stimulating proteins, cell surface receptors, accessory signaling molecules, transport proteins, enzymes, anti-bacterial and/or anti-viral proteins or polypeptides, and the like, depending on the intended use of the ultimate composition.

The biomaterials of the invention with three-dimensional patterned surfaces allow location-controlled mineralization and cellular deposition. The three-dimensional, surface-patterned biomaterials of the present invention are "smart biomaterials", which preferentially bind biological molecules and cells in specific locations. The region-specific surface properties allow control over the location and activity of cells attaching to the biomaterial, when used both in cell culture and in in vivo implantation.

These aspects of the invention represent an important advance, as control over the "locations" of cell deposition and activity is envisioned to be at least as important as controlling the "characteristics" of cell activity. In fact, controlling the location of active cells on the surface of a biomaterial may prove to be the most important determinant in tissue regeneration. The techniques of the present invention are particularly advantageous as they provide the ability to control the locations of cell presence and activity on the surface of a biomaterial on a micron scale.

A. Extended Mineral Formation

Certain aspects of the present invention are processes for altering a biomaterial by growing an extended or homogeneous mineral layer on the surface. Porous, degradable, polymer biomaterials are preferred for such processes, e.g., polylactic acid (PLA), polyglycolic acid (PGA) and polylactic-co-glycolic acid (PLGA).

The inventors' rationale behind coating these materials with minerals is that mineral-like coatings are important for bone growth into a porous material and/or for adhesion to a substrate. The basis for this process lies in the observation that in nature, organisms use various macromolecules to control nucleation and growth of mineral phases (Campbell et al., 1996; Lowenstein and Weiner, 1989). These macromolecules usually contain functional groups that are negatively charged at the crystallization pH (Weiner, 1986). It is hypothesized that these groups chelate ionic species present in the surrounding media, stimulating crystal nucleation (Campbell et al., 1996).

Observations on natural mineralization processes have not previously been adapted for use in connection with biomaterials or tissue engineering processes. However, the present inventors realized that a biomaterial substrate could be functionalized in the laboratory to allow the induction of mineral deposition.

The inventors further realized that the presence of an extended or homogeneous mineral layer on the surface of a biomaterial will aid in the ability to effectively regenerate bone tissue. Described herein are various methods for achieving such extended or homogeneous surface mineralization. However, patterned (or heterogeneous) surface mineralization is also contemplated for use in certain embodiments, and may be advantageously achieved by the patterning techniques disclosed herein.

B. Controlling Locations of Cell Activity

Recent advances in the control of cellular processes have shown the utility of controlling the characteristics of cell activity. However, such work has not addressed the specific control of locations of cell adhesion to a biomaterial. The present inventors envision the control over "locations" of cell activity to be as important as control of the characteristics of cell activity.

Specifically, in the area of bone tissue regeneration, a prerequisite for biomaterials to bond to living bone is the formation of a bone-like mineral layer on the biomaterial in the body. This observation suggested to the inventors that the presence or absence of the mineral may determine whether or not bone cells will adhere to and subsequently act on a biomaterial. Thus, they reasoned that specific control over the location of mineral on a biomaterial surface will allow control over locations of bone cell activity. Patterning of minerals on the surface of a biomaterial should therefore have a profound effect on the properties of regenerated bone tissue.

In order to control the locations of cell adhesion to a three dimensional polymer surface, the present invention further provides several new methods of treating biopolymers prior to cell seeding. In a surprisingly simple method, pre-treating only certain regions or sub-sections of biopolymer materials, matrices or scaffolds with mineral-containing aqueous solutions results in localized mineralization in only those areas in contact with the mineralizing solution. Treatment of the polymer biomaterials on a micron scale is preferably accomplished using one of two different processes: surface photolysis and/or surface electrolysis.

The patterned photolysis and electrolysis methods of the present invention are suitable for use with porous, biodegradable polymer scaffolds. The surface manipulation methods of the present invention are surprising in that the inventors' adaptation of techniques from the electron beam lithography field has allowed, for the first time, patterning applications on three dimensional biomatrices, rather than being limited to two dimensions. Three dimensional matrices are generally more effective for creating a biomaterial scaffold for use in tissue regeneration.

The various patterning techniques of the invention therefore provide the ability to control locations for bone cells specifically (mineral patterning), and for all cell types in general (polymer surface treatment without mineral formation). The differences in processing for control of bone cells versus control of other cell types are described herein.

As also described in the Detailed Examples, all processes of the present invention are room temperature processes. Therefore, specific bioactive substances, drugs and proteins, such as adhesion molecules, cytokines, growth factors and the like, can be incorporated into the patterning process and resultant biomaterial. Proteins can also be incorporated into the cell culture medium, thus patterning the material surface and causing attachment of specific cells.

C. Photolysis

Certain methods of the invention for functionalizing the surface a biomaterial to allow mineralization and/or control of cellular location are based upon radiation processes (with or without patterning). To achieve a homogeneous mineral layer on a biomaterial surface, radiation processes without patterning are used. To achieve control of cellular location or mineralization, patterned radiation processes are used.

The treatment of polymer biomaterials with electromagnetic (EM) radiation causes surface degradation via a photolysis reaction. Suitable radiation includes all wavelengths of EM radiation, including ultraviolet, visible, infrared, etc. This form of surface degradation, like that achieved with NaOH, causes an increase in the amount of polar oxygen functional groups on the surface of the material.

Interpreting results from distinct studies on bone bonding polymers (Li et al. 1997), me inventors reasoned that the polar oxygen groups formed would spur mineral nucleation on the surface of the biomaterial when placed in a body fluid. Thus, the inventors realized that the ability to pattern three dimensional surface functional groups would result in the ability to pattern mineral formation and cell adhesion on the surface of a biomaterial.

Unfortunately, the EM radiation techniques formerly available were all limited to applications with two dimensional objects. Conventional "contact" optical lithography techniques are so-limited (to two dimensions) due to the requirement for close contact between a mask or contact grating and the object to be patterned. Thus, prior to the present invention, there was no mechanism for producing surface patterns on the type of three dimensional, surface-contoured materials that are of most use in tissue engineering.

Lithographic techniques are based upon passing monochromatic EM radiation through an optical grating to produce radiation patterns on a screen that is on the opposite side of the grating from the EM radiation source. The pattern formed can be as simple as equally spaced fringes formed by a grating containing equally spaced slits, or as complicated as a complex hologram.

The present invention significantly advances the tissue engineering art by providing methods for using EM radiation to pattern three dimensional biopolymers. In the inventive methods, the "screen" is the polymer biomaterial. This system amounts to a "diffraction lithography" approach, but the process differs from conventional "contact" optical lithography in that the grating does not act as a mask for the polymer, so that near contact between the grating and the polymer is not necessary.

In the present methods, the grating produces a pattern of constructive and destructive interference on the polymer surface. As the grating is not required to be in near contact with the biomaterial during treatment, this diffraction lithography process can be used to treat materials with complex three-dimensional surface contours. This is also a surprising application of previous technology in that the technique now employed would sacrifice line width when used in previous embodiments, so, absent the inventors' particular insight regarding three dimensional matrix patterning, there would be no motivation to develop this methodology. Further, the "contact mask" does not need to be removed, improving the sterile nature of the biotechnique.

Certain types of three dimensional biomatrices envisioned for patterning using this invention are microsphere and cylindrical matrices. Although a motivation for developing the present invention was the inventors' goal to develop a process for three dimensional and contoured patterning, now that the process has been developed, it is equally suitable for use with two dimensional polymers.

D. Electrolysis

The treatment of polymer biomaterials with electron beam (e-beam) irradiation can also be used to cause surface degradation via an electrolysis reaction. Surface degradation effects an increase in the amount of polar oxygen functional groups on the surface of the material, which have the same advantageous qualities described herein for the hydrolysis and photolysis reactions.

Surface electrolysis can be patterned on a polymer surface using a scanning electron microscope with basic e-beam lithography capabilities. As shown in the Detailed Examples, this process can also be used to treat materials with flat surfaces or complex three-dimensional surface contours.

E. Chemical Hydrolysis

Other methods for surface-functionalizing a biomaterial to allow mineral deposition utilize chemical pre-treatment to achieve surface hydrolysis, e.g., using a NaOH solution. Surface degradation by this technique causes an increase in the amount of polar oxygen functional groups on the surface of the material. The functionalized surface is then incubated in a mineral-containing solution. The inventors have used such functionalization techniques to allow the generation of a mineral coating or "hypermineralization".

Gao et al. (1998) recently reported the surface hydrolysis of poly(glycolic acid) meshes in order to increase the seeding density and improve attachment of vascular smooth muscle cells. Although their procedure was also based upon the hydrolysis of PGA in NaOH, the polymer scaffold was then directly progressed to the cell seeding experiments (Gao et al., 1998). The present invention instead exposes the surface-hydrolyzed biopolymer to a calcium-rich solution to induce surface mineralization.

F. Combined Chemical Hydrolysis and Mineralization

In an unexpected development of the surface-functionalization methods, the inventors surprising found that effective mineral deposition could be achieved on biomaterial surfaces without chemical pre-treatment. In these methods, a degree of surface hydrolysis sufficient to allow mineralization occurs by simply soaking the biomaterial in an aqueous mineralizing medium. Although pre-treatment, such as by exposure to a NaOH solution, may still be utilized or even preferred in certain embodiments, the one-step mineralization processes have the advantage of simplicity and are preferred in certain embodiments.

The one-step mineralization methods utilize the same type of mineral-containing aqueous solutions as described above, such as body fluids and synthetic media that mimic body fluids. Functionalization is followed by mineralization in situ, without external manipulation. Although these methods are suitable for use with a wide range of biopolymers, the current preferences are for use in conjunction with PLG copolymers with ratios in the region of 85:15 PLG copolymers, and with biomaterial scaffolds prepared by gas-foaming/particulate leaching processes. The use of 85:15 PLG copolymer scaffolds prepared by gas-foaming/particulate leaching is particularly preferred.

The use of 85:15 PLG copolymers is advantageous as a decrease in the lactide/glycolide ratio of the copolymer is believed to increase the rate of surface hydrolysis. However, prior to the present invention, the use of 85:15 PLG copolymers was disfavored as the mechanical integrity of the polymer declines with increasing glycolide content. This invention shows that 85:15 PLG copolymers can be used effectively as the rapid surface hydrolysis allows sufficient mineral formation to offset the potential for decreasing integrity, resulting in a sufficient or even increased overall strength of the composite.

The successes of the present one step mineralization methods (Example V), even without foaming/particulate leaching, are in marked contrast to previous attempts to grow minerals on polyester surfaces. The earlier methods do not result in growth of continuous bone like mineral layers, even after a 6 day incubation in fluids with 50% higher ionic concentrations than presently used (Tanahashi et al., 1995). Equally, a 15 day incubation in essentially the same media fluid as presently used failed to produce continuity of mineral microparticles (Zhang and Ma, 1999).

The inventors believe that matrix preparation via gas foaming/particulate leaching techniques results in more surface carboxylic acid groups than matrix preparation by other methods (e.g., solvent casting/particulate leaching). This greater surface functionalization is proposed to contribute to the more rapid nucleation and growth of apatitic mineral observed during the one-step mineralization processes. Also, the leaching steps of the gas foaming/particulate leaching methods typically employ mineral solutions, such as 0.1 M $CaCl_2$, which may further facilitate $Ca^{2+}$ chelation and more rapid bone-like mineral nucleation.

The techniques of matrix formation by gas foaming/particulate leaching, with or without additional bioactive agents, are described in the following co-owned applications, each of which are incorporated herein by reference without disclaimer: U.S. patent application Ser. No. 09/402,119, filed Sep. 20, 1999, which claims priority to PCT Application No. PCT/US98/06188 (WO 98/44027), filed Mar. 31, 1998, which designates the United States and claims priority to U.S. Provisional Application Ser. No. 60/042,198, filed Mar. 31, 1997; and U.S. application Ser. No. 09/310,802, filed May 12, 1999, which claims priority to second provisional application Ser. No. 60/109,054, filed Nov. 19, 1998 and to first provisional application Ser. No. 60/085,305, filed May 13, 1998.

The studies in Example IX show that bone-like mineral can be advantageously formed on the inner pore surfaces of matrices prepared by gas foaming/particulate leaching. PLG scaffolds prepared by a gas foaming/particulate leaching process were successfully mineralized using a one step incubation in simulated body fluid (SBF) without any appreciable decrease in total scaffold porosity.

Using gas foamed/particulate leached PLG scaffolds, a 5 day incubation in SBF is sufficient for continuous growth of bone-like mineral on the inner pore surfaces of the scaffold (Example IX). Quantification of percent mass gain and phosphate content suggests that the majority of mineral growth in these aspects of the invention occurs between day 2 and day 4 of incubation. These results are even more advanced over the previous attempts to produce bone-like minerals on polyester surfaces (Tanahashi et al., 1995; Zhang and Ma, 1999).

As these one-step mineralization processes are effective at room temperatures, their use to prepare mineralized or hypermineralized polymer scaffolds extends to the preparation of mineralized materials that include other bioactive substances. It is demonstrated herein that such processes are not detrimental to the activity of biological molecules, such as growth factors. The time- and labor-saving nature of these processes therefore make them ideal for preparing matrices for use in many biological processes, especially to stimulate bone growth, where minerals and growth factors act in concert. The phase, morphology and constitution of the deposited mineral can be controlled by varying the pH, ionic concentrations and/or temperatures used in the process.

These mineralization techniques are particularly suitable for use with biodegradable materials. The ability to obtain a continuous bone-like mineral layer within the pores of a three dimensional, porous, degradable scaffold represents a breakthrough in biomaterial processing. The growth of such a continuous bone-like mineral layer is not only important to cell seeding, but will also likely increase the mechanical integrity of these synthetic constructs via a reinforcement mechanism.

Polymer constructs used for tissue engineering applications are generally highly porous and do not have mechanical properties in the same range as bone. Creating an interconnected mineral coating over the inner pore surfaces of a polymer construct, according to these aspects of the present invention, is therefore a distinct advantage. These methods allow for the production of a hard and stiff exoskeleton, increasing the modulus of a biomaterial and enhancing its resistance to cellular contractile forces during tissue development.

The mineralized scaffold materials of the present invention, e.g., as produced in Example V, in fact have a post-treatment compressive modulus larger than those of other poly(α-hydroxy acid) materials used for bone tissue engineering and larger than PLLA bonded poly(glycolic acid) (PGA) matrices that are adequate for resistance of cellular forces during smooth muscle tissue development. The materials of this inventory therefore exhibit shape memory, an important factor in tissue regeneration. The present invention also provides methods to achieve increases in compressive moduli without notably decreasing scaffold porosity or pore size, another long-sought after design advantage that allows cellular migration and vascular infiltration.

G. Mineralization and Growth Factor Release

In addition to showing successful mineralization using a one step, five day incubation, the studies of Example IX also demonstrate the sustained release of a bioactive factor (VEGF) from mineralized PLG scaffolds. Three dimensional, porous scaffolds of the copolymer 85:15 poly(lactide-co-glycolide) were fabricated by including the growth factor into a gas foaming/particulate leaching process. The scaffold was then mineralized via incubation in a simulated body fluid.

To summarize, the growth of a bone like mineral film on the inner pore surfaces of the porous scaffold is confirmed by mass increase measurements and quantification of phosphate content within scaffolds. Release of $^{125}$I-labelled VEGF was tracked over a 15 day period to determine release kinetics from the mineralized scaffolds. Sustained release from the mineralized scaffolds was achieved, and growth of the mineral film altered the release kinetics from the scaffolds by attenuating the initial burst effect, and making the release curve more linear. The VEGF released from the mineralized and non-mineralized scaffolds was over 70% active for up to 12 days following mineralization treatment, and the growth of mineral had little effect on total scaffold porosity.

Figure 7:
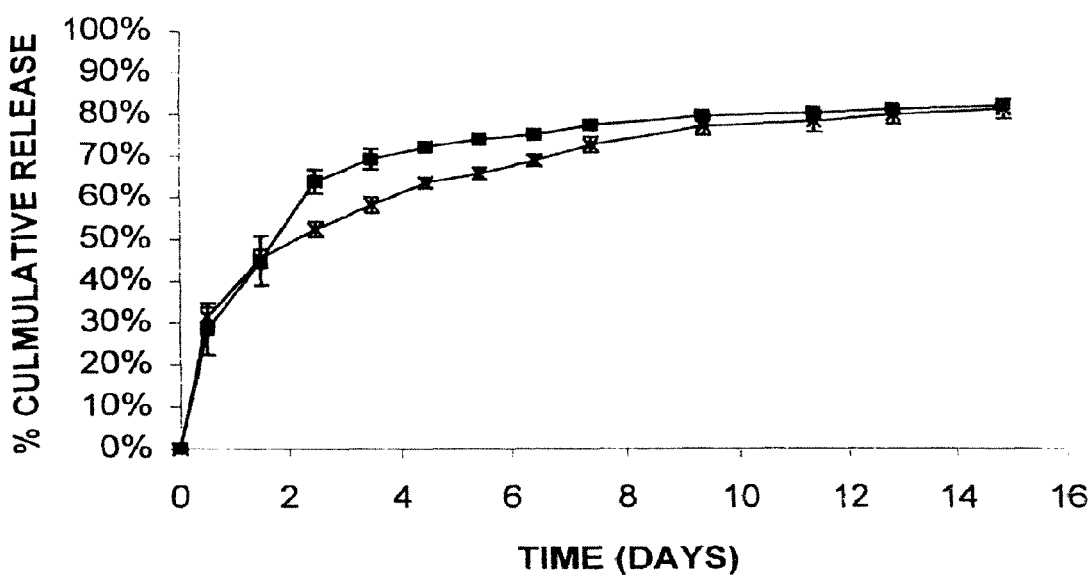
FIG. 7. Cumulative release of vascular endothelial cell growth factor (VEGF) from mineralized (X) and non-mineralized ■ scaffolds. Values represent mean and standard deviation (n=5).

In more detail, the mineral presence is shown to slow the release of the growth factor from the scaffold, resulting in release of a greater amount of factor for a longer time period (e.g., days 3 through 10). After an initial burst release of 44±2% of the incorporated factor in the first 36 h, the release profile is sustained from the mineralized sponges for up to 10 days in SBF (FIG. 7). In contrast, the release from the non-mineralized scaffolds shows a relatively large initial burst of 64±2% over the first 60 h, followed by sustained release for ~5 days.

The release of a bioactive factor from a mineralized scaffold is an important result for tissue engineering, particularly bone tissue engineering, because it combines the osteoconductive qualities of a bone-like mineral with the tissue inductive qualities of a bioactive factor, such as a protein growth factor. VEGF release is specifically useful in the induction of vascular tissue ingrowth for tissue engineering. This system could also be used with a variety of other inductive protein growth factors, easily matched to the cell and tissue types intended to be stimulated.

Example IX suggests that the growth of mineral on the surface of porous PLG modulates factor release. There is a clear correlation between the onset of mineral growth and the divergence in the release profiles for samples incubated in SBF and PBS (control). The former occurs between day 2 and day 4 of incubation (FIG. 6), while the latter occurs at the 3 day time point (FIG. 7). The net effect of mineral presence is attenuation of the initial burst release from the scaffold, and sustained release of a larger amount of factor for a longer period of time.

Figure 8A:
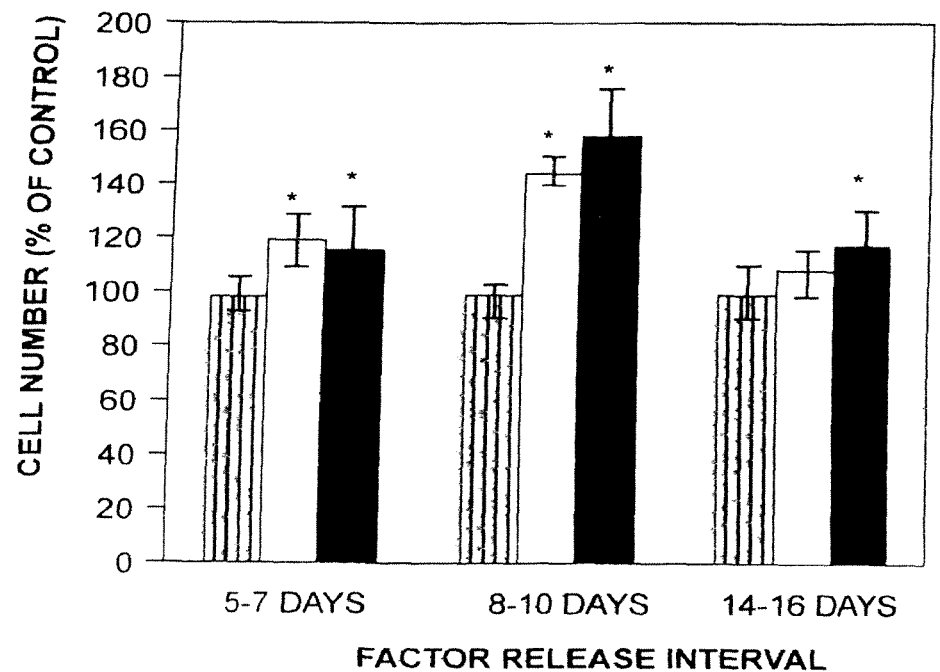
FIG. 8A. Stimulatory effect of VEGF release from mineralized ■ and non-mineralized (□) scaffolds on human dermal microvascular endothelial cells. Cell counts for each release time interval are given as percents of the control value (striped column) for that interval. Values that are significantly larger than their corresponding control are indicated by *'s. Values represent mean and standard deviation (n=5).

The release modulation effect is also apparent in the bioactivity data (FIG. 8A). Release from the mineralized scaffolds has a significantly greater effect on cell proliferation than release from the non-mineralized scaffolds during the factor release interval 8-10 days. Examination of the release profiles (FIG. 7) indicates that the mineralized scaffolds release a larger amount of VEGF than the non-mineralized scaffolds during this period.

Previous controlled release formulations using poly($\alpha$-hydroxy acid) materials frequently demonstrate a sizeable initial burst in the first 1-5 days of release followed by minimal release at later time points (Cohen et al., 1991; Kwong et al., 1986). Achieving relatively constant release over a longer period of time is a substantial goal in polymeric drug delivery. Previous attempts to address the "burst effect" have used double-walled polymer microspheres (Pekarek et al., 1994) and microspheres encapsulated in microporous membranes (Kreitz et al., 1997). The bone-like mineral in this study achieves a functional effect similar to the outer layer in double-walled polymeric drug delivery systems.

The formation of a mineral layer within the pores of PLG scaffolds does not notably impair the ability of released growth factor to stimulate proliferation of human dermal microvascular endothelial cells. The possibility of protein denaturation and aggregation upon exposure to moisture is a concern in the controlled release of proteins from certain polymer systems (Ishaug-Riley et al., 1998). In this case, the protein is clearly bioactive for eleven days after mineralization treatment (16 days after sample preparation).

The 11 day time scale was chosen for analysis in this study because a large percentage of transplanted cells fail to engraft and die within this time period without the development of a vascular supply to augment mass transport (Mooney et al., 1997; Ishaug-Riley et al., 1998). Sustained release over this time scale induces increased proliferation of endothelial cells, thus supporting angiogenesis during the initial stages of osseous tissue development in vivo.

The present invention therefore provides a system for the sustained release of bioactive factors, such as polypeptides, growth factors and hormones, from mineralized PLG scaffolds. The mineral-biofactor-scaffolds have particular uses in orthopaedic tissue engineering. The presence of a bone-like mineral is a prerequisite to conduction of osteogenic cells into various porous synthetic constructs (Hench, 1991; Kokubo, 1991), and so the mineral is associated with increased bioreactivity (LeGeros and Daculzi, 1990). The mineral grown by the methods of the present invention thus provides enhanced osteoconductivity in addition to the inductive (e.g., angiogenic) effect of protein release. The growth of the mineral is accomplished via a surprisingly simple single step, room temperature process which, importantly, does not compromise growth factor bioactivity, or total scaffold porosity.

The following examples are included to demonstrate certain preferred embodiments of the invention. It will be appreciated by those of skill in the art that the compositions and techniques disclosed in the examples that follow represent compositions and techniques discovered by the inventor to function well in the practice of the invention, and thus can be considered to constitute certain preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Homogeneous Surface Mineralization

A porous, degradable polymer biomaterial is treated for substantially homogeneous mineralization by either pre-treating to induce surface hydrolysis and then exposing to a mineralizing solution (Examples II through IV) or by conducting a one-step surface hydrolysis and mineralization process (Example V).

Pre-treatment to produce homogeneous surface hydrolysis may be achieved by either soaking in a NaOH solution (Example II) or by treating with electromagnetic (EM) radiation (Example III). The treated biomaterial is incubated in a mineral-rich, preferably a calcium-rich, fluid, such as a body fluid or synthetic media that mimics body fluid, to spur nucleation and growth of a homogeneous mineral film on the surface (Example IV).

Functionalization and concomitant mineralization can also be achieved by simply soaking in mineral-containing aqueous solutions, preferably in body fluids or synthetic media that mimic body fluids. Preparation of the polymer biomaterials using a gas-foaming/particulate leaching process is generally preferred for such one step mineralization (Example V).

Once mineralized, osteogenic cell precursors are seeded onto the biomaterial in vitro in a cell culture medium. In vivo, bone cells attach to the biomaterial when implanted.

EXAMPLE II

NaOH Pre-Treatment for Surface Mineralized Films

PLGA films (~25 μm thickness) were prepared by a pressure casting technique. Raw polymer pellets were loaded into a mold and placed in a convection oven at 200 degrees C. The molds were heated under pressure (~22 N) for 30 sec. and then cooled to room temperature.

For the creation of surface functional groups by NaOH treatment, the films were cleansed and immersed in 1.0 N NaOH solution for varying times, up to 10 minutes to create surface functional groups. Following immersion, samples were rinsed 3× in distilled water.

EXAMPLE III

UV Pre-Treatment for Surface Mineralized Films

PLGA films (~25 μm thickness) were prepared by a pressure casting technique. Raw polymer pellets were loaded into a mold and placed in a convection oven at 200 degrees C. The molds were heated under pressure (~22 N) for 30 sec. and then cooled to room temperature.

For the creation of surface functional groups by UV (ultra violet) treatment, membranes were exposed to up to 8 hrs of surface irradiation.

EXAMPLE IV

Surface Mineralization after Pre-Treatment

Membranes treated by either NaOH treatment or UV treatment were subsequently incubated at 37 degrees C. in 50 ml of a simulated physiological fluid (SPF, Na: 142 mM, K: 5 mM, Ca: 2.5 mM, Mg: 1.5 mM, Cl: 148 mM, HCO3: 4.2 mM, HPO4: 1 mM, SO4: 0.5 mm) buffered to pH 7.4. Solutions were replaced every 48 hours to ensure that there were sufficient ions in solution to induce mineral nucleation and growth. Following immersion for periods of 120 to 240 hours, samples were dried.

Fourier transform infrared (FTIR) analysis indicates the presence of a surface amorphous apatite. FTIR spectra of scaffolds treated for 0, 2, 6, 10, and 16 days indicate the growth of a carbonated apatite mineral within the scaffold (FIG. 1). Equivalent spectra were also produced with the LTV-treated films. The broad band at 3570 cm$^{-1}$ is indicative of the stretching vibration of hydroxyl ions in absorbed water. The peak at 1454 cm$^{-1}$ is indicative of $CO_3^{2-}v_3$, while the 867 cm$^{-1}$ represents $CO_3^{2-}v_2$. The peaks at 1097 cm$^{-1}$ and 555 cm$^{-1}$ are indicative of anti-symmetric stretch ($v_3$) and anti-symmetric bending ($v_4$) of $PO_4^{3-}$, respectively. The peak at 1382 cm$^{-1}$ represents a $NO_3$ band.

The presence of $OH^-$, $CO_3^{2-}$ and $PO_4^{3-}$ all indicate that an apatitic layer has been formed. Other bands representative of apatites are masked because of the strong absorption of the PLGA.

The major peaks at 1755 cm$^{-1}$ and 1423 cm$^{-1}$ represent PLGA, and the peak at 1134 cm$^{-1}$ is indicative of C—O stretch in the ester. The peaks at 756 cm$^{-1}$ and 956 cm$^{-1}$ are indicative of the amorphous domains of the polymer.

Figure 2:
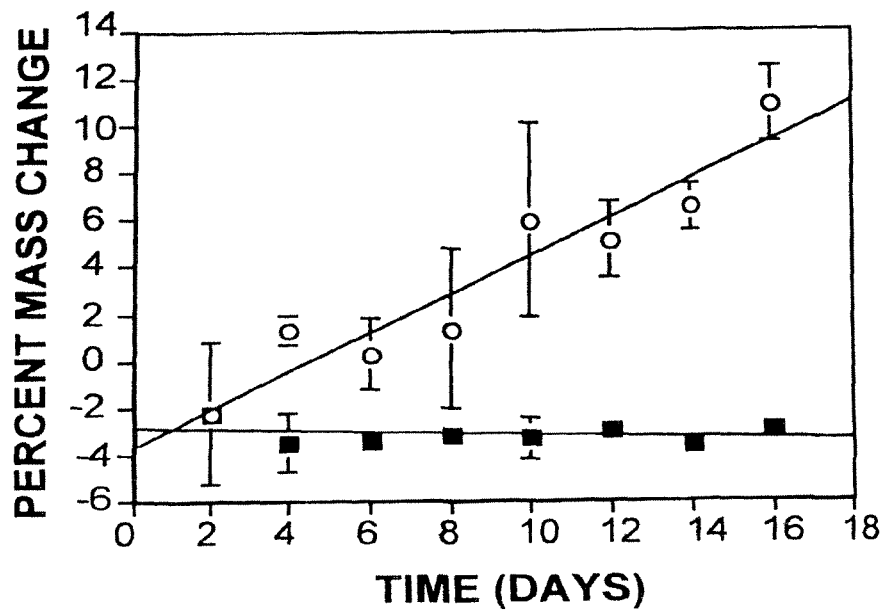
FIG. 2. Percent mass increase vs. incubation time of scaffolds incubated in SBF (o), and (■) control samples incubated in Tris buffer (pH=7.4). Graph shows a trend of increasing mass of SBF-incubated scaffolds, culminating in a 11+/−2% mass increase after a 16 day incubation.

The scaffolds demonstrated an increase in mass over time, culminating in a 11±2% mass gain at the end of the 16 day incubation (FIG. 2). ANOVA of percent mass changes of experimental scaffolds reveal a significant difference in scaffold mass over time ($p<0.05$), while ANOVA of percent mass changes of control scaffolds does not show a significant difference over time ($p>0.05$). Percent mass changes of experimental samples and control samples were significantly different for each time point beyond 8 days ($p<0.05$).

Figure 3:
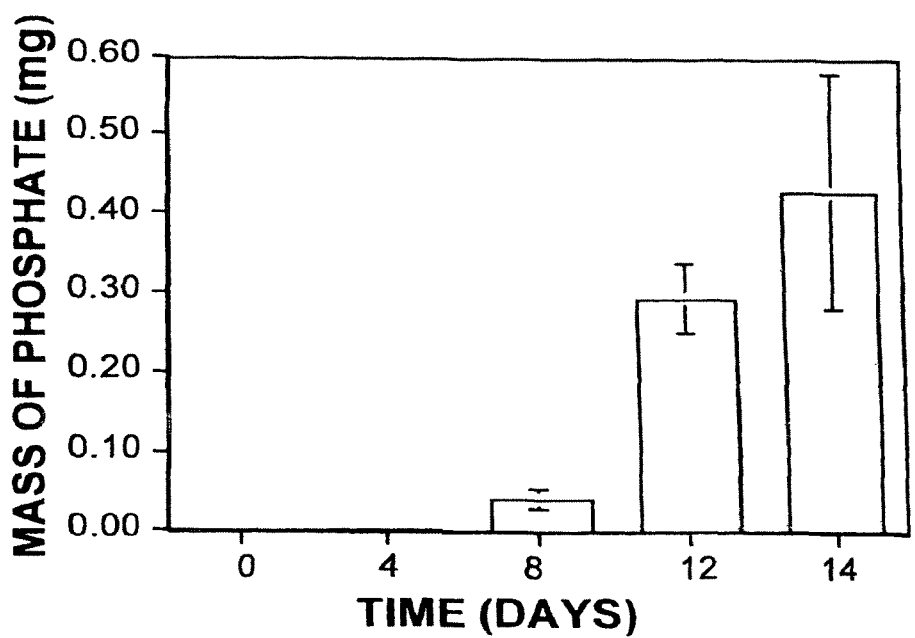
FIG. 3. The mass of phosphate present in the scaffolds vs. incubation time.

To confirm that the increase in mass was caused by deposition of an apatitic mineral, the mass of phosphate in the scaffolds was next analyzed. Phosphate content within the treated scaffolds also increased significantly with the treatment time (FIG. 3). Comparison of phosphate masses via ANOVA show a statistically significant increase over time ($p<0.05$), and the differences in phosphate mass between day 8 and 12 ($p<0.05$) and between day 12 and 14 ($p=0.05$) were also statistically significant. After a 14 day incubation, estimation of the mass of mineral on the scaffold using phosphate mass data gives 0.76 mg of hydroxyapatite, while the measured mass increase of the scaffold is 1.02±0.40 mg. The fact that the measured value is larger than the estimated value suggests significant carbonate substitution in the mineral crystal.

Figure 4:
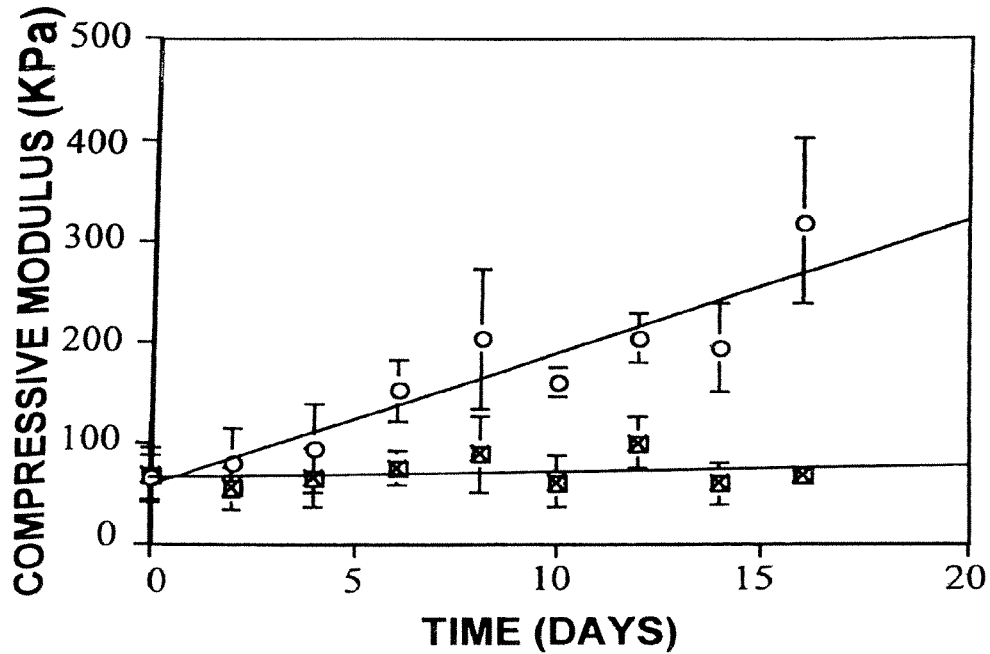
FIG. 4. Compressive modulus vs. incubation time for scaffolds incubated in SBF (o), and control scaffolds incubated in Tris buffer (pH=7.4) (▨).

Growth of the BLM layer significantly increased the compressive modulus of 85:15 PLG scaffolds (FIG. 4) without a significant decrease in scaffold porosity. The compressive modulus increased from 60±201 KPa before treatment to 320±60 KPa after a 16 day treatment, a 5-fold increase in modulus. ANOVA of modulus changes of experimental scaffolds reveal a significant difference in scaffold modulus over time ($p<0.05$), while ANOVA of control modulus data does not show a significant difference over time ($p>0.05$). The differences between moduli of experimental scaffolds and moduli of control scaffolds were statistically significant for treatment times of 10 days or longer ($p<0.05$). The porosity of the scaffolds did not decrease appreciably after incubation in SBF. Untreated scaffolds were 95.6±0.2% porous, while scaffolds incubated in SBF for 16 days were 94.0±0.30% porous (n=3). This agrees with the electron micrographs, which displayed only a thin (1-10 μm) mineral coating, and thus no significant change in pore size due to mineral growth.

This example shows the successful use of this room temperature process to yield an apatitic surface layer upon a treated polymer surface. The importance of room temperature processing is that attachment of biological factors is readily achievable, without concern for denaturation.

EXAMPLE V

One Step Mineralization

One step, room temperature incubation processes can also be used to cause nucleation and growth of mineral layers on polymer surfaces. This is achieved by incubating polymer scaffolds in mineral-containing aqueous solutions, such as body fluids and synthetic media that mimic body fluids. These processes are able to grow bone-like minerals within polymer scaffolds in surprisingly simple and inexpensive methods. The effectiveness of these methods under room temperature conditions renders them conducive to the inclusion of bioactive proteins and other materials into the processing mineralization.

A first example of one step mineralization concerns the mineral deposition on porous poly(lactide-co-glycolide) sponges via incubation in a simulated body fluid. The simple incubation technique was used to obtain nucleation and growth of a continuous carbonated apatite mineral on the interior pore surfaces of a porous, degradable polymer scaffold.

A 3-dimensional, porous scaffold of 85:15 PLG was fabricated by a solvent casting/particulate leaching process and incubated in simulated body fluid (SBF; NaCl-141 mM, KCl-4.0 mM, $MgSO_4$-0.5 mM, $MgCl_2$-1.0 mM, $NaHCO_3$-4.2 mM, $CaCl_2$-2.5 mM, and $KH_2PO_4$-1.0 mM in deionized $H_2O$, buffered to pH=7.4 with Trisma-HCl). Fourier transform IR spectroscopy and SEM analyses after different incubation times demonstrated the growth of a continuous bone-like apatite layer within pores of the polymer scaffold.

The majority of the mineral growth occurred between days 8 and 12. Mineral growth into a continuous layer likely occurs from day 12, and is complete at or before day 16. The mineral grown, being continuous, is thus similar to that in bones and teeth.

The scaffolds demonstrated an increase in mass over time, with an 11±2% gain after 16 days. The increase in mass is due to deposition of an apatitic material. Quantification of phosphate on the scaffold revealed the growth and development of the mineral film over time with an incorporation of 0.43 mg of phosphate (equivalent to 0.76 mg of hydroxyapatite) per scaffold after 14 days in SBF. The measured overall mass increase of the scaffold was 1.02±0.4 mg at 14 days. This suggests carbonate substitution in the mineral crystal.

The compressive moduli of polymer scaffolds also increased fivefold with formation of a mineral film after a 16 day incubation time, as opposed to control scaffolds. This was achieved without a significant decrease in scaffold porosity. The thin mineral coating is thus functionally important, yet mineralization does not change the pore size.

As shown in the mineralization and growth factor studies of Example IX, 85:15 PLG scaffolds prepared by gas foaming/particulate leaching exhibit even more rapid nucleation and growth of apatitic mineral. The 85:15 PLG scaffolds prepared via solvent casting/particulate leaching showed a 3±1% increase in mass after a 6 day incubation in SBF. In comparison, 85:15 PLG scaffolds prepared by gas foaming/particulate leaching showed a mass increase of 6±1% after a 4 day incubation in SBF.

The even more rapid nucleation and growth of apatitic mineral on 85:15 PLG scaffolds prepared by gas foaming/particulate leaching is believed to be due to the increase in carboxylic acid groups caused by the gas foaming/particulate leaching process, i.e., the greater surface functionalization. Leaching with 0.1 M $CaCl_2$ also likely facilitates chelation of $Ca^{2+}$ ions, producing more rapid bone-like mineral nucleation.

EXAMPLE VI

Bone Cell Control

Polymer biomaterial is treated to form a patterned biosurface, preferably suing either patterned EM radiation or electron beam irradiation. Treated biomaterial is washed with distilled water to remove residual monomers from the surface photolysis or electrolysis.

The treated biomaterial is incubated in a mineral-rich, preferably a calcium-rich, fluid, such as a body fluid or synthetic media that mimics body fluid, to spur nucleation and growth of mineral on the treated regions of the polymer. This results in a mineral pattern on the surface of the polymer. This step can be done either in vitro, using a body fluid or simulated body fluid; or in vivo, where the natural body fluid performs this function.

Osteogenic cell precursors are seeded onto the biomaterial in vitro in a cell culture medium. In vivo, bone cells attach to the biomaterial when implanted. In either case, cells adhere preferentially to mineralized portions of the substrate.

EXAMPLE VII

Diffraction Lithography

Previous studies on the control of locations of cell adhesion to a biomaterial surface have utilized conventional UV lithography to pattern a two dimensional polymer surface (Pierschbacher & Ruoslahti, 1984); Ruoslahti & Pierschbacher, 1987); Matsuda et al., 1990); Britland et al., 1992); Dulcey et al., 1991); Lom et al., 1993); Lopez et al., 1993); Healy et al., 1996).

In the prior techniques, the two-dimensional biomaterial surface is coated with a thin layer of photoresist (PR), the PR is exposed through a metal mask, and the exposed PR is removed in solvent, leaving a PR mask on the surface of the biomaterial sample. The surface of the polymer biomaterial is then chemically or physically treated through the PR mask, and the mask is removed by a solvent after treatment.

The former processes requires a flat, two dimensional biomaterial, which suffices for studying the effects of surface treatment on cell activity, but is not sufficient for the treatment of typical biomaterials, which have three dimensional surface contours.

In the present methods, suitable for use with three dimensional polymers, the grating produces a pattern of constructive and destructive interference on the polymer surface. As the grating is not required to be in near contact with the biomaterial during treatment, this diffraction lithography process can be used to treat materials with complex three-dimensional surface contours. However, the process is equally useful in connection with two dimensional biomaterials.

EXAMPLE VIII

Control of Other Cell Types

Polymer biomaterial is treated to form a patterned biosurface, preferably using either patterned EM radiation or electron beam irradiation. Treated biomaterial is washed with distilled water to remove residual monomers from the surface photolysis or electrolysis.

The treated biomaterial is incubated in a solution containing bioactive molecules or proteins, such as growth factors, adhesion molecules, cytokines and such like, which promote adhesion of a specific cell type. Cells are seeded onto the biomaterial in vitro in a cell culture medium. In vivo, cells attach to the biomaterial when implanted. In either case, cells adhere preferentially to the treated portions of the substrate.

The use of specific agents or proteins, such as growth factors, that promote attachment of certain cell types, gives the potential to pattern any cell type on the three dimensional surface of the polymer, both in vitro and in vivo.

EXAMPLE IX

Growth Factor Release from Mineralized Matrices

A. Materials and Methods
1. Gas Foaming-Particulate Leaching

Poly(lactide-co-glycolide) pellets with a lactide:glycolide ratio of 85:15 were obtained from Medisorb, Inc. (I.V.=0.78 dl/g) and ground to a particle size between 106 and 250 µm. Ground PLG particles were then combined with 250 µl of a 1% alginate (MVM, ProNova: Oslo, Norway) solution in $ddH_2O$, and 3 µg of vascular endothelial cell growth factor (VEGF, Intergen; Purchase, N.Y.), and vortexed. These solutions were lyophilized, mixed with 100 mg of NaCl particles (250 µm<d<425 µm), and compression molded at 1500 psi for 1 min in a 4.2 mm diameter die. This yielded 2.8 mm thick disks with a diameter of 4.2 mm.

Disks were then exposed to 850 psi $CO_2$ gas in an isolated pressure vessel and allowed to equilibrate for 20 h. The pressure was decreased to ambient in 2 min, causing thermodynamic instability, and subsequent formation of gas pores in the polymer particles. The polymer particles expand and conglomerate to form a continuous scaffold with entrapped alginate, VEGF, and NaCl particles. After gas foaming, the disks were incubated in 0.1 M $CaCl_2$ for 24 h to leach out the salt particles and induce gellation of the alginate within the polymer matrix. Alginate was included in the scaffolds because it has been shown to abate the release of VEGF from PLG scaffolds (Wheeler et al., 1998).
2. Mineralization Certain scaffolds were mineralized via a 5 day incubation in a simulated body fluid (SBF). Simulated body fluid (SBF)

was prepared by dissolving the following reagents in deionized $H_2O$: NaCl-141 mM, KCl-4.0 mM, $MgSO_4$-0.5 mM, $MgCl_2$-1.0 mM, $NaHCO_3$-4.2 mM, $CaCl_2$-2.5 mM, and $KH_2PO_4$-1.0 mM. The resulting SBF was buffered to pH=7.4 with Trisma-HCl and held at 37° C. during the incubation periods. The SBF solutions were refreshed daily to ensure adequate ionic concentrations for mineral growth.

The porosity of scaffolds was calculated before and after mineralization treatment using the known density of the solid polymer, the known density of carbonated apatite, the measured mass of mineral and polymer in the scaffolds, and the volume of the scaffold.

3. Characterization of Mineral Growth

To analyze mineral growth on gas foamed PLG scaffolds, sets of three scaffolds were incubated in SBF for periods ranging from 0-10 days. Samples were removed from solution and analyzed after 0, 2, 4, 8, and 10 day incubation periods. The dry mass of each scaffold was measured before and after incubation in SBF, and percent increases in mass were calculated and compared using ANOVA and a Student's t-test to reveal significant differences in mass for different SBF incubation times.

The amount of phosphate present in the scaffolds after the aforementioned incubation times was determined using a previously described colorimetric assay (Murphy et al., *J. Biomed. Mat. Res.*, In Press; incorporated herein by reference). The phosphate mass data were also compared using ANOVA and a Student's t-test to reveal significant differences in mass for different SBF incubation times.

To estimate the amount of apatite on the scaffold after a 6 day incubation, the measured mass of phosphate was multiplied by the known ratio of mass of hydroxyapatite $[Ca_{10}(PO_4)_6(OH)_2$, f.w.=1004.36 g] to mass of phosphate in hydroxyapatite (569.58 g). This is a conservative estimate, since it assumes that all phosphate is being incorporated into stoichiometric hydroxyapatite. This mineral mass estimate increases if one assumes increasing substitution of carbonate into the mineral crystal.

4. VEGF Release Measurements

In order to assess the incorporation efficiency of VEGF into the PLG scaffolds and to track the VEGF release kinetics from the scaffolds, receptor-grade $^{125}I$-labeled human VEGF (90 µCi/µg; Biomedical Technologies Inc.; Stoughton, Mass.) was utilized as a tracer. In place of the 3 µg VEGF in the normal sample preparation, 0.5 µCi of radiolabeled VEGF was added to each matrix. To assess VEGF incorporation efficiency, the total incorporated activity was compared to the activity of the initial $^{125}I$ VEGF sample prior to incorporation into the scaffolds.

To determine the effects of mineral growth on factor release, release kinetics were measured both in SBF during mineral formation and in phosphate buffered saline (PBS). Scaffolds prepared with radiolabeled VEGF were placed in 4 ml of SBF or PBS and held at 37° C. At various set times, the scaffolds were removed from solution and their radioactivity was assessed using a gamma counter. After each analysis, solutions were refreshed and scaffolds were placed back into solution.

The amount of radiolabeled VEGF released from the scaffolds was determined at each time point by comparing the remaining $^{125}I$ VEGF to the total originally loaded into each scaffold. The percent release of VEGF from scaffolds incubated in SBF was compared to that of scaffolds incubated in PBS at each time point via a Student's I-test to reveal significant differences in cumulative release.

5. Biological Activity of Released VEGF

The biological activity of VEGF incorporated into, and released from, polymer matrices was determined by testing its ability to stimulate the growth of cultured human dermal microvascular endothelial cells isolated from neonatal dermis (HMVEC(nd), Cascade Biologics; Portland, Oreg.).

HMVEC(nd) were cultured to passage 7 in MCDB 131 media (Cascade Biologics) supplemented with Cascade Biologics' microvascular growth supplement (5% fetal bovine serum, hydrocortisone, human fibroblast growth factor, heparin, human epidermal growth factor, and dibutyryl cyclic AMP) prior to use. Cells were plated at a density of $5 \times 10^3$ cells/cm$^2$ on 12 well tissue culture dishes (Corning; Cambridge, Mass.) which were precoated with 1 µg/cm$^2$ human plasma fibronectin (Life Technologies, Grand Island, N.Y.). The cells were allowed to attach for 24 h, and the media in each well was replaced then with 3 ml of serum-free media (Cell Systems; Kirkland, Wash.) supplemented with 50 µg/ml gentamicin (Life Technologies).

A 12 mm transwell (3 µm pore diameter, Corning) containing either mineralized, or non-mineralized, VEGF releasing matrix was placed in each experimental well (n=5 for each group), while mineralized matrices containing no VEGF were placed in the control wells (n=5). To determine the dose response to known concentrations of VEGF, additional wells (n=4 per concentration) were supplemented with 40, 20, 10, and 5 ng/ml of soluble VEGF which had not been incorporated into matrices.

After 72 h all of the cells in the experimental and control wells were removed with a solution of 0.05% trypsin/0.53 mM EDTA (Life Technologies), and counted using a ZM Coulter counter (Coulter; Miami, Fla.). The transwells containing matrices were immediately transferred to new fibronectin-coated (1 µg/cm$^2$) wells that had been seeded with cells ($5 \times 10^3$ cells/cm$^2$) 24 h before, and allowed to incubate for an additional 72 h before the cells were removed and counted. A new set of VEGF dose response wells were also set up concurrent with the transfer of the transwells. The 72 h cycles were continued for 12 days.

Cell counts in experimental wells were compared to cell counts in control wells for each 72 h interval using a Student's t-test to reveal significant differences in HMVEC proliferation.

B. Results

1. Mineralization

Figure 5:
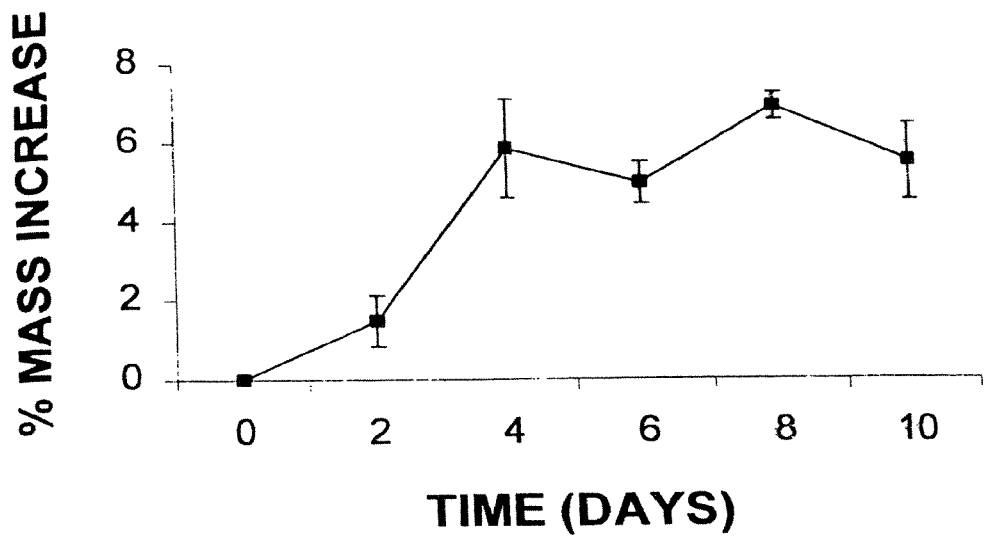
FIG. 5. Percent mass increase vs. incubation time for PLG scaffolds incubated in simulated body fluid (SBF). Values represent mean and standard deviation (n=3).

Incubation of gas foamed 85:15 poly(lactide-co-glycolide) scaffolds containing VEGF resulted in the growth of bone-like mineral on the inner pore surfaces. Analysis of variance showed that differences in percent mass gain with SBF incubation time were significant (p<0.05). The scaffolds showed an increase in mass with incubation time, with a 6±1% mass gain after a 4 day incubation in SBF (FIG. 5). The scaffold mass subsequently remained relatively constant. The increase in mass between two day and four day incubation times was significant (p<0.05), while there was no significant difference in percent mass gain between the four day incubation time and the longer incubation times (p>0.05).

Figure 6:
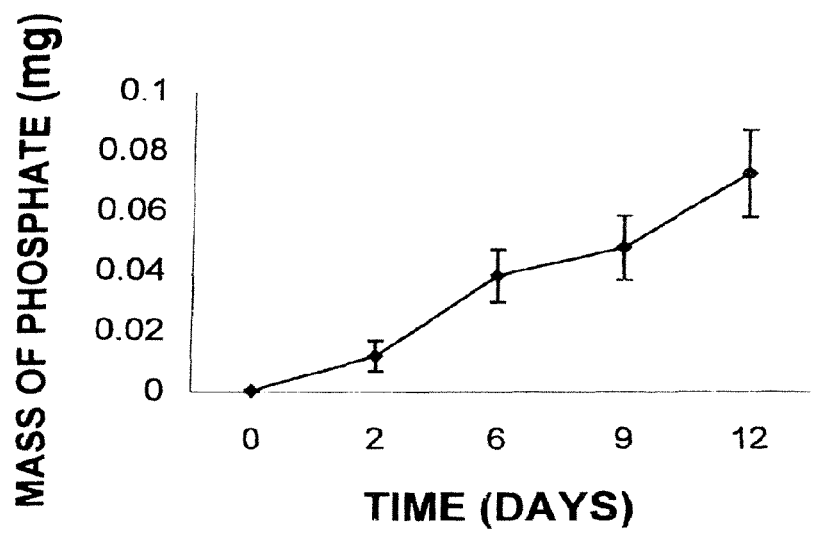
FIG. 6. The mass of phosphate present in scaffolds vs. incubation time in SBF. Values represent mean and standard deviation (n=3).

To verify that the increase in mass was caused by the deposition of an apatitic mineral, the mass of phosphate in the scaffolds was analyzed. Phosphate content within scaffolds increased with SBF incubation time (FIG. 6). Analysis of variance showed that differences in phosphate content with SBF incubation time were significant (p<0.05). The difference in phosphate content between the two day and six day incubation times was significant (p<0.05), while there was no significant difference between the phosphate mass of the six day incubation time and longer incubation times ($p>0.05$).

The inventors have previously shown that the increase in mass and phosphate content in these scaffolds indicates growth of a continuous bone-like mineral film on the inner pore surfaces (Murphy et al., *J. Biomed. Mat. Res.*, In Press).

The total porosity of the scaffolds after a 10 day incubation in SBF was 92±1%, which is similar to the initial scaffold porosity (93±1%).

After a 6 day incubation, estimation of the mass of mineral on the scaffold using phosphate mass data gives 0.10 mg of hydroxyapatite, while the measured mass increase of the scaffold is 0.39±0.03 mg. The fact that the measured value is larger than the estimated value suggests significant carbonate substitution in the mineral crystal.

2. VEGF Release and Activity

Vascular endothelial cell growth factor (VEGF) was incorporated into PLG scaffolds with an efficiency of 44±9% and released over a 15 day period in SBF and PBS solutions. An initial burst release of the incorporated growth factor was observed over the first 12-36 h followed by a sustained release for the remainder of the study (FIG. 7).

The cumulative release from scaffolds incubated in SBF became significantly smaller than release from scaffolds incubated in PBS after 3 days, and this difference remained significant through 10 days of release ($p<0.05$). At time points beyond 10 days there is no significant difference in cumulative release from scaffolds incubated in SBF versus those incubated in PBS ($p>0.05$).

VEGF released from mineralized and non-mineralized scaffolds had a mitogenic effect on human dermal microvascular endothelial cells (HMVECs).

Cells were grown in wells containing three different scaffold types: 1) Mineralized, VEGF-containing scaffolds (MV scaffolds); 2) non-mineralized, VEGF containing scaffolds (NV scaffolds); and 3) mineralized control scaffolds without VEGF (MC scaffolds). Cells grown in wells containing MV and NV scaffolds demonstrated significantly increased proliferation when compared with cells grown in wells containing MC scaffolds (FIG. 8A). Cell counts were significantly higher in wells containing MV and NV scaffolds for all time intervals ($p<0.05$) with the exception of the wells containing NV scaffolds over the 14-16 day factor release interval.

During the 8-10 day factor release interval, MV scaffolds showed a significantly greater mitogenic effect on HMVECs than NV scaffolds ($p<0.05$). There was no significant difference in the stimulatory effect of MV scaffolds versus NV scaffolds for any other time interval ($p>0.05$).

Figure 8B:
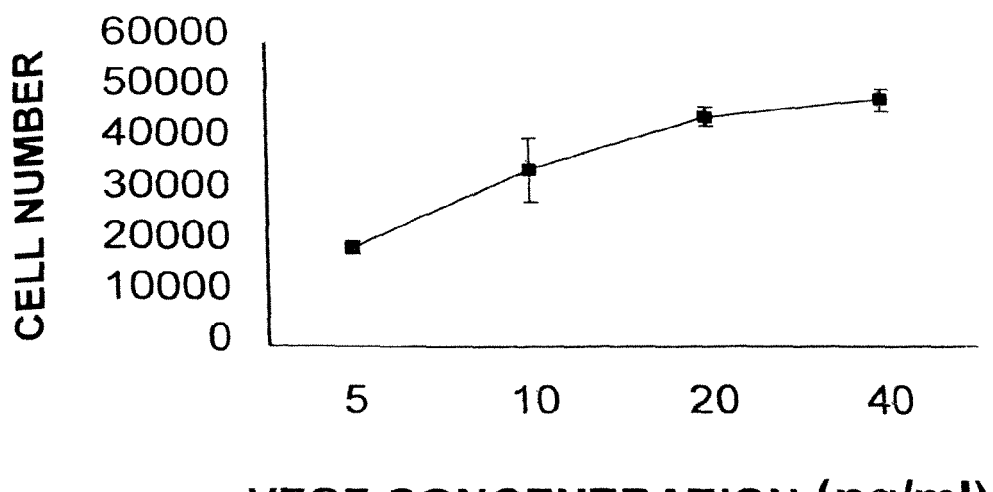
FIG. 8B. Sample dose-response curve demonstrating the mitogenic effect of VEGF on human dermal microvascular endothelial cells. Values represent mean and standard deviation (n=5).

A dose-response curve (FIG. 8B) generated for the HMVECs was used to calculate an effective concentration for the released growth factor. Comparison of this effective concentration with the amount of VEGF known to be released during each time interval (FIG. 7) indicates that the released VEGF is over 70% active for all time intervals.

EXAMPLE X

Effects of Growth Factors on Mineralization

A. Materials and Methods

Poly(lactide-co-glycolide) pellets with a lactide:glycolide ratio of 85:15 were obtained from Medisorb, Inc. (I.V.=0.78 dl/g) and ground to a particle size between 106 and 250 p.m. Ground PLG particles were then combined with 250 μl of a 1% alginate (MVM, ProNova; Oslo, Norway) solution in ddH$_2$O, and vortexed. These solutions were lyophilized, mixed with 100 mg of NaCl particles (250 μm<d<425 μm), and compression molded at 1500 psi for 1 minute in a 4.2 mm diameter die. This yielded 2.8 mm thick disks with a diameter of 5.0 mm.

Disks were then exposed to 850 psi CO$_2$ gas in an isolated pressure vessel and allowed to equilibrate for 20 hours. The pressure was decreased to ambient in 2 minutes, causing thermodynamic instability, and subsequent formation of gas pores in the polymer particles. The polymer particles expand and conglomerate to form a continuous scaffold with entrapped alginate, and NaCl particles. After gas foaming, the disks were incubated in 0.1 M CaCl$_2$ for 24 hours to leach out the salt particles and induce gellation of the alginate within the polymer matrix. Alginate was included in the scaffolds because it has been used in VEGF release studies to help abate the release of VEGF from PLG scaffolds, and it was necessary to precisely mimic the scaffold conditions during factor release studies.

The total porosity of scaffolds was calculated using the known density of the solid polymer, the measured mass polymer in the scaffold, and the measured volume of the scaffold. Cross sectional electron micrographs of scaffolds were obtained by bisecting the scaffolds via freeze fracture and imaging using a Hitachi S3200N scanning electron microscope.

To assess the effect of VEGF in solution on the mineral growth process, scaffolds were incubated in SBF containing 0.2 μCi $^{125}$I VEGF (Receptor grade human VEGF, 90 μCi/μg, Biomedical Technologies Inc.; Stoughton, Mass.) (n=5). Samples were incubated for five days, since this is the time period required for growth of a significant amount of bone-like mineral within the inner pore surfaces of gas foamed/particulate leached 85:15 PLG scaffolds. After incubation, scaffolds were washed three times in ddH$_2$O, and assessed for radioactivity using a gamma counter. The percent incorporation of VEGF into the polymer scaffolds was calculated (Counts of scaffold/counts of solution*100) and plotted vs. incubation time.

The incubation was done in tubes that were siliconized using sigmacote, then presoaked in a 1% bovine serum albumin (BSA) solution for 30 minutes to coat the tube surface with BSA and thus reduce binding of VEGF to the inner surface of the tubes. Solutions were refreshed daily to ensure sufficient ionic concentrations for mineral growth and constant concentration of the iodinated growth factor in the solution.

Simulated body fluid (SBF) was prepared daily by dissolving the following reagents in deionized H$_2$O: NaCl-141 mM, KCl-4.0 mM, MgSO$_4$-0.5 mM, MgCl$_2$-1.0 mM, NaHCO$_3$-4.2 mM, CaCl$_2$-2.5 mM, and KH$_2$PO$_4$-1.0 mM. The resulting SBF was buffered to pH=7.4 with Trisma-HCl and held at 37° C. during the incubation periods.

B. Results

85:15 Poly(lactide-co-glycolide) scaffolds prepared via a gas foaming/particulate leaching process were 93±1% porous and displayed an open pore structure with a pore diameter of ~200 μm.

Figure 9:
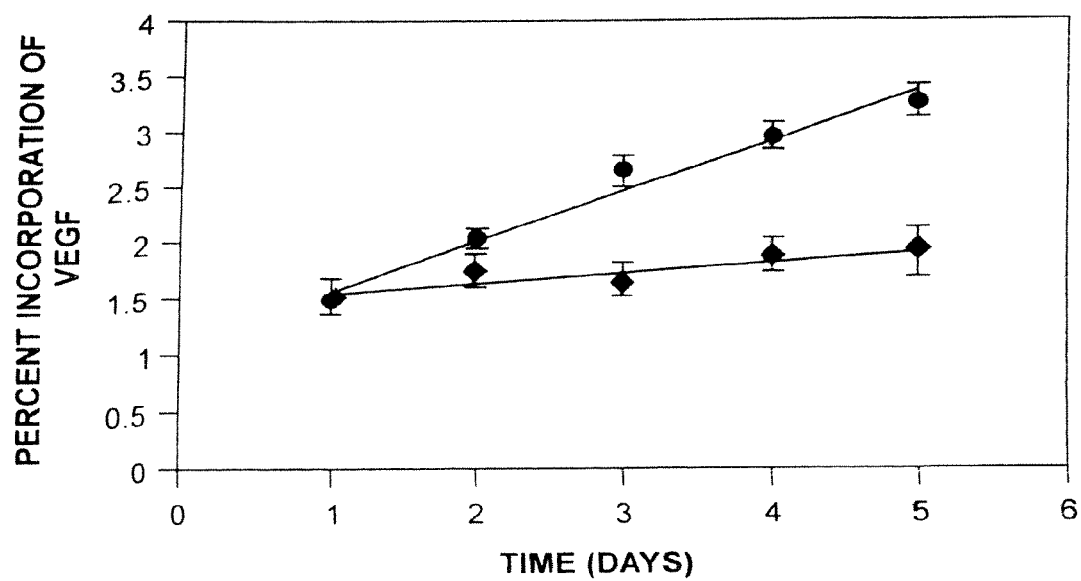
FIG. 9. Incorporation of VEGF into PLG scaffolds during incubation in SBF (♦) and Tris-HCl buffer (○).

The incorporation of radioactive VEGF into the scaffolds was larger for control scaffolds than for experimental scaffolds for all time points beyond 2 days ($p<0.05$). The control data also show a trend of increasing incorporation of VEGF with increasing incubation time (FIG. 9). These data indicate that VEGF is being incorporated into the control scaffolds more efficiently than it is being incorporated into the experimental samples, and the amount of VEGF in the experimental scaffolds is not increasing during mineralization treatment.

The data show that VEGF does not significantly incorporate into PLG scaffolds during incubation in SBF. There is also no significant incorporation of the growth factor into the mineral during the initial stages of mineral growth. Thus, the previously shown attenuation of VEGF release from PLG scaffolds during mineral growth cannot be explained by incorporation of protein into the mineral film, binding of the protein to the scaffold surface, or diffusion of the protein back into the scaffold during protein release.

The postulated steps in the mineral growth process on PLG scaffolds are: 1) surface functionalization via a hydrolysis reaction; 2) Chelation of $Ca^{2+}$ ions by surface carboxylate anions; 3) Nucleation and growth of mineral crystals on the polymer surface. The lack of incorporation of VEGF into PLG scaffolds incubated in SBF indicates that the protein does not compete with calcium ions for binding sites on the inner pore surfaces of the scaffolds or efficiently diffuse back into the scaffolds after release.

In this case, the amount of protein incorporated into the scaffolds was significantly larger for control samples incubated in Tris-HCl buffer, and the incorporation increased over time. The increased efficiency of incorporation of VEGF into control samples may be due to more efficient diffusion of the factor into control scaffolds, or enhanced binding of the factor to the inner pore surfaces of the control scaffolds. This result shows that the effects of mineral growth on VEGF release from PLG scaffolds cannot be explained incorporation of VEGF back into PLG scaffolds after release, or binding of VEGF to the scaffold's inner pore surfaces.

There is no significant incorporation of protein into the mineral film during the initial stages of mineral growth. During incubation of PLG scaffolds in SBF containing $^{125}I$ VEGF. the amount of VEGF measured in the scaffolds did not change significantly after day 2. The present study limited the time frame for SBF incubation to 5 days, since this was a period in which mineral growth was initiated, and significant mineral growth occurred in a previous study on gas foamed/particulate leached 85:15 PLG scaffolds.

Previous studies on mineralized PLG scaffolds show that mineral growth continues for at least two weeks in vitro and it considered that bioactive factors may incorporate into the mineral film for longer incubation periods. Notably, the attenuation of the release of VEGF from PLG scaffolds caused by mineral formation cannot be explained by incorporation of the protein into the mineral film, since this attenuation occurs primarily within the first 5 days of SBF incubation, and there is no significant incorporation during this time period.

Because the attenuation of growth factor release from PLG scaffolds cannot be explained by incorporation of proteins back into the scaffolds after release, or incorporation of proteins into the growing mineral crystals, it is likely that the attenuation is simply due to a barrier effect. The mineral crystal growing on the inner pore surfaces of the PLG scaffold may physically block the release of proteins from the polymer matrix. This barrier effect has been studied extensively in controlled drug delivery applications using layered polymeric microspheres and microspheres encapsulated in microporous membranes, and the growth of bone-like mineral represents a new method for blocking protein diffusion out of polymeric materials.

Thus, vascular endothelial growth factor does not incorporate into the mineral film or significantly incorporate into the polymer scaffold during incubation of PLG in SBF. The previously observed effect of mineral growth on VEGF release from PLG scaffolds is likely caused by the mineral acting as a physical barrier to protein diffusion out of the scaffold. This mechanism is contemplated to be useful in controlled drug delivery applications, as the release profile from these materials could be predictably controlled by mineral film thickness and density.

All of the compositions and methods disclosed and claimed herein can be made and executed without undue experimentation in light of the present disclosure. While the compositions and methods of this invention have been described in terms of certain preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abe, Kokubo, Yamamuro. "Apatite coating on ceramics, metals, and polymers utilizing a biological process". *J. Mater. Sci. Mater. Med.,* 1:233 (1990).

Britland, Perez-Arnaud, Clark, McGinn, Connolly, Moores, "Micropatterning proteins and synthetic peptides on solid supports: a novel application for microelectronics fabrication technology," *Biotechnol. Prog.,* 8:155-160, 1992.

Byung-Soo and Mooney, "Engineering smooth muscle tissue with a predefined structure," *J. Biomed. Mat. Res.,* 1997.

Campbell, Fryxell, Linehan, Graff, "Surface-induced mineralization: a new method for producing calcium phosphate coatings," *J. Biomed. Mat. Res.,* 32:111-118, 1996.

Cohen, Yoshioka, Lucarelli, Hwang, Langer, "Controlled delivery systems for proteins based on Poly(Lactic/Glycolic Acid) microspheres," *Pharmaceutical Research,* 8:713-720, 1991.

Colton, "Implantable biohybrid artificial organs," *Cell Transplant,* 4:415-436, 1995.

Crane, Ishaug, Mikos, "Bone Tissue Engineering," *Nat. Med.,* 1:1322-1324, 1995.

Dulcey, Georger, Krauthamer, Stenger, Fare, Calvert, Deep, "Photochemistry of chemisorbed monolayers: patterned coplanar molecular assemblies," *Science,* 252:551-554, 1991.

Gao, Niklason, Langer, "Surface hydrolysis of poly(glycolic acid) meshes increases the seeding density of vascular smooth muscle cells," *J. Biomed. Mat. Res.,* 42:417-424, 1998.

Giannobile, "Periodontal tissue engineering by growth factors," *Bone,* 19:23S-37S, 1996.

Gilding, "Biodegradable Polymers," *In: Biocompatibility of Clinical Implant Materials,* Williams, D F, (ed.), CRC Press, Boca Raton, Fla., pp. 209-232, 1981.

Harris, Kim, Mooney "Open pore biodegradable matrices formed with gas foaming," *J. Biomed. Mat. Res.*, 42:396-402, 1998.

Healy, Thomas, Rezania, Kim, McKeown, Lom, Hockberger, "Kinetics of bone cell organization and mineralization on materials with patterned surface chemistry," *Biomat.*, 17:195-208, 1996.

Hench, "Bioceramics: from concept to clinic," *J. Am. Ceram. Soc.*, 74:1487-1510, 1991.

Hench, "Bioceramics: From concept to clinic," *J. Am. Ceram. Soc.*, 74:1487-1510, 1991;

Kokubo, "Recent progress in glass based materials for biomedical applications," *J. Ceram. Soc. Jpn.*, 99:965-973, 1991.

Ishaug-Riley, Crane, Gurlek, Miller, Yaszemski, Yasko, Mikos, "Ectopic bone formation by marrow stromal osteoblast transplantation using poly(DL-lactic-co-glycolic acid) foams implanted into the rat mesentery," *J. Biomed. Mat. Res.*, 36:1-8, 1997.

Ishaug-Riley, Crane-Kruger, Yaszemski, Mikos "Three-dimensional culture of rat calvarial osteoblasts in porous biodegradable polymers," *Biomaterials*, 19:1405-1412, 1998.

Kim and Mooney, "Engineering smooth muscle tissue with a predefined structure," *J. Biomed. Mat. Res.*, 41:322-332, 1998.

Kohn, Renier, Eaton, Carter, "Environmentally-Responsive Polyamide-Acrylate Grafts Modulate Ion-Exchange," *J. Biomed. Mat. Res*, 1997.

Kokubo, "Recent progress in glass-based materials for biomedical applications," *J. Ceram. Soc. Jpn.*, 99:965-973, 1991.

Kreitz, Webber, Galletti, Mathiowitz, "Controlled delivery of therapeutics from microporous membranes: II. In vitro degradation and release of heparin-loaded poly(D,L-lactide-co-glycolide)," *Biomaterials*, 18:597-603, 1997.

Kwong, Chou, Sun, Sefton, Goosen, "In vitro and in vivo release of insulin from poly(lactic acid) microbeads and pellets," *J. Cont. Rel.*, 4:47-62, 1986.

Langer, "New methods of drug delivery," *Science*, 249:1527-1532, 1990.

Langer and Vacanti, "Tissue Engineering," *Science*, 260:920-926, 1993.

LeGeros and Daculzi, "In vivo transformation of biphasic calcium phosphate ceramics: Ultrastructural and physicochemical characterizations," In: *Handbook of Bioactive Ceramics*, CRC Press, Inc., Boca Raton, p. 17-28, 1990.

Leung, Cachianes, Kuang, Goeddel, Ferrara, "Vascular endothelial growth factor is a secreted angiogenic mitogen," *Science*, 246:1306-1309, 1989.

Li, Garreau, Vert, "Structure property relationships in the case of the degradation of massive poly($\alpha$-hydroxy acids) in aqueous media," *J. Mat. Sci. Mat. Med.*, 1:123-139, 1990.

Li, Bakker, van Blitterswijk, "The bone bonding polymer Polyactive 80/20 induces hydroxycarbonate apatite formation in vitro," *J. Biomed. Mat. Res.*, 34:79-86, 1997.

Lo, Ponticiello, Leong, "Fabrication of controlled release biodegradable polymer foams by phase separation," *Tissue Engineering*, 1:15-28, 1995.

Lom, Healy, Hockberger, "A versatile technique for patterning biomolecules onto glass substrates," *J. Neurosci. Meth.*, 50:385-397, 1993.

Lopez, Albers, Schreiber, Carroll, Peralat, Whitesides, "Convenient methods for patterning the adhesion of mammalian cells to surfaces using self assembled monolayers of alkanethiolates on gold," *J. Am. Chem. Soc.*, 115:5877-5878, 1993.

Lowenstein and Weiner, "On Biomineraliztion," Oxford Univ. Press, Oxford, 1989.

Mikos, Sarakinos, Ingber, Vacanti, Langer, "Prevascularization of porous biodegradable polymers," *Biotechnology and Bioengineering*, 42:716-723, 1993.

Mikos and Thorsen, "Preparation and characterization of poly(L-lactic acid) foams," *Polymer*, 35:1068-1077, 1994.

Minabe, "A critical review of the biologic rationale for guided tissue regeneration," *J. Periodontol*, 62:171-179, 1991.

Mooney, Kaufmann, Sano, McNamara, Vacanti, Langer, "Transplantation of hepatocytes using porous, biodegradable sponges," *Transplant Proc.*, 26:3425-3426, 1994.

Mooney, et al., "Long term engraftment of hepatocytes transplanted on biodegradable polymer sponges," *J. Biomed. Mat. Res.*, 37:413-420, 1997.

Murphy, Kohn, Mooney "Growth of continuous bone-like mineral within porous poly(lactide-co-glycolide) scaffolds in vitro," *J. Biomed. Mat. Res.*, In Press.

Pekarek, Jacob, Mathiowitz, "Double-walled polymer microspheres for controlled drug release," *Nature*, 367:258-260, 1994.

Pierschbacher and Ruoslahti, "Cell attachment activity of fibronectin can be duplicated by small synthetic fragments of the molecule," *Nature*, 309:30-33, 1984.

Poss, R., Ed. *Orthopaedic Knowledge Update*, Vol. 3. (American Academy of Orthopaedic Surgeons, Chicago, 1990.)

Putnam and Mooney, "Tissue engineering using synthetic extracellular matrices," *Nat. Med.*, 2:824-826, 1996.

Ripamonti, "Calvarial reconstruction in baboons with porous hydroxyapatite," *J. Craniofac. Surg.*, 3:149-159, 1992.

Ruoslahti and Pierschbacher, "New perspectives in cell adhesion: RGD and integrins," *Science*, 238:491-497, 1987.

Shea, Smiley, Bonadio, Mooney, "DNA delivery from polymer matrices for tissue engineering," *Nat. Biotech.*, 17:551-554, 1999.

Shea, Wang, Francheschi, Mooney, "Bone formation from pre-osteoblasts on 3-D scaffolds," Submitted.

Sheridan, Shea, Peters, Mooney, "Bioabsorbable polymer scaffolds for tissue engineering capable of sustained growth factor delivery," *J. Cont. Rel.*, In Press.

Tanahashi, Yao, Kokubo, Minoda, Miyamoto, Nakamura, Yamamuro, "Apatite coated on organic polymers by biomimetic process: Improvement in adhesion to substrate by glow discharge treatment," *J. Biomed Mat. Res.*, 29:339-347, 1995.

Weiner, "Organization of extracellularly mineralized tissues: a comparative study of biological crystal growth," *CRC Crit. Rev. Biochem.*, 20:365-408, 1986.

Whang, Tsai, Nam, Aitken, Sprague, Patel, Healy, "Ectopic bone formation via rhBMP-2 delivery from porous bioabsorbable polymer scaffolds," *J. Biomed. Mat. Res.*, 42:491-499, 1998.

Wheeler, Chamberland, Schmitt, Buck, Brekke, Hollinger, Joh, Suh, "Radiomorphometry and biomechanical assessment of recombinant human bone morphogenetic protein 2 and polymer in rabbit radius ostectomy model, 43:365-373, 1998.

Zhang and Ma, "Porous poly(L-lactic acid)/apatite composites created by biomimetic process," *J. Biomed. Mat. Res.*, 45:285-293, 1999.

The invention claimed is:

1. A method for controlling mineralization of a biomaterial surface, comprising:
   (a) functionalizing at least a first surface of a biomaterial; and
   (b) contacting the functionalized biomaterial surface with an amount of a mineral-containing solution effective to form a mineralized biomaterial,
   wherein
      (i) the mineralized biomaterial comprises an extended, mineral coating at the functionalized biomaterial surface and is degradable over a controllable time scale; and
      (ii) the biomaterial comprises at least a first porous, biodegradable polymer portion having an interconnected pore structure and further comprises at least a first portion that is prepared by a process comprising heating a biodegradable polymer.

2. The method of claim 1 wherein heating the biodegradable polymer in a heat pressing process.

3. The method of claim 1 wherein the polymer portion of the biomaterial is a poly(alpha-hydroxy acid).

4. The method of claim 1 wherein the functionalizing of at least a first surface of a biomaterial creates a plurality of polar oxygen groups on the biomaterial surface.

5. The method of claim 1 wherein said mineral coating is osteoconductive.

6. The method of claim 1 wherein the biomaterial is associated with a biologically effective amount of at least a first bioactive substance or biological cell.

7. A method for controlling mineralization of a biomaterial surface, said method comprising:
   (a) forming a biomaterial by heating a biodegradable polymer, said biomaterial comprising at least a first porous, biodegradable polymer portion that has an interconnected pore structure;
   (b) functionalizing a first surface of said biomaterial; and
   (c) contacting the functionalized biomaterial surface with an amount of a mineral-containing solution effective to form a mineralized biomaterial that comprises an extended, mineral coating at the functionalized biomaterial surface.

8. The method of claim 7 wherein the forming a biomaterial by heating a biodegradable polymer comprises heat pressing.

9. The method of claim 7 wherein said biodegradable polymer is a poly(alpha-hydroxy) acid.

10. The method of claim 7 wherein the functionalizing a first surface of said biomaterial creates a plurality of polar oxygen groups on the biomaterial surface.

11. The method of claim 7 wherein said mineral coating is osteoconductive.

12. The method of claim 7 wherein the biomaterial is associated with a biologically effective amount of at least a first bioactive substance or biological cell.

13. A method for generating an extended, osteoconductive mineral coating on a surface of a porous, biodegradable polymer biomaterial, comprising:
   contacting a surface of said porous, biodegradable polymer biomaterial with an amount of a mineral-containing solution effective to form an extended, osteoconductive mineral coating on said surface, wherein
      said porous, biodegradable polymer biomaterial has an interconnected pore structure and is degradable over a controllable time scale; and
      said biomaterial comprises at least a first portion that is prepared by a process comprising heating a biodegradable polymer.

14. The method of claim 13 wherein heating is heat pressing.

15. The method of claim 13 wherein the biodegradable polymer is poly(alpha-hydroxy) acid).

16. The method of claim 13 further comprising exposing at least a first surface of said biomaterial to a functionalizing pre-treatment to create a functionalized biomaterial surface prior to contacting the biomaterial surface with an amount of a mineral-containing solution.

17. The method of claim 16, wherein the functionalized biomaterial surface is contacted with said mineral-containing solution for a time effective to form discrete mineral islands that expand to form a substantially homogeneous, osteoconductive mineral coating.

18. The method of claim 13 wherein the biomaterial surface is part of a 3-dimensional biomaterial scaffold.

19. The method of claim 13 wherein the biomaterial is associated with a biologically effective amount of at least a first bioactive substance or biological cell.

20. The method of claim 16 wherein said biodegradable polymer biomaterial is a poly(alpha-hydroxy) acid.

* * * * *